United States Patent [19]
Svendsen et al.

[11] Patent Number: 5,914,306
[45] Date of Patent: Jun. 22, 1999

[54] STABILIZED ENZYMES

[75] Inventors: Allan Svendsen, Birkerød; Claus von der Osten, Lyngby; Ib Groth Clausen, Charlottenlund; Shamkant Anant Patkar, Lyngby; Kim Borch, Copenhagen, all of Denmark

[73] Assignee: Novo Nordisk A/S, Bagsvaerd, Denmark

[21] Appl. No.: 08/140,008

[22] PCT Filed: May 1, 1992

[86] PCT No.: PCT/DK92/00142

§ 371 Date: Oct. 22, 1993

§ 102(e) Date: Oct. 22, 1993

[87] PCT Pub. No.: WO92/19726

PCT Pub. Date: Nov. 12, 1992

[30] Foreign Application Priority Data

May 1, 1991 [EP] European Pat. Off. .............. 91610035

[51] Int. Cl.[6] .............................. C11D 3/386; C12N 9/20
[52] U.S. Cl. .......................... 510/392; 510/530; 435/188; 435/209
[58] Field of Search ....................... 252/174.12, DIG. 12, 252/198, 209; 510/392, 530; 435/188, 209

[56] References Cited

U.S. PATENT DOCUMENTS 4,738,682   4/1988   Boegh et al. ............................... 8/401

FOREIGN PATENT DOCUMENTS 0305216   3/1989   European Pat. Off. .
89/01520   2/1989   WIPO .
8901520    2/1989   WIPO .
8906278    7/1989   WIPO .
8909263   10/1989   WIPO .
9117243   11/1991   WIPO .

OTHER PUBLICATIONS

Chou et al, J. Mol. Biology β—*Turns in Proteins* vol. 115, pp. 135–175, 1977.

T.E. Greighton, J. Mol. Biol. *Implications of Many Proline Residues for Kinetics of Protein Folding and Unfolding*, vol. 125, pp. 401–406, 1978.

M. Levitt, Preferences of Amino Acids, vol. 17, No. 20, 1978.

*Primary Examiner*—Kery Fries
*Attorney, Agent, or Firm*—Steve T. Zelson; Elias J. Lambiris

[57] ABSTRACT

This invention relates to novel stabilized enzymes. More specifically the invention relates to novel stabilized enzymes, in which a naturally occurring amino acid residue (other than proline) has been substituted with a proline residue at one or more positions; at which position(s) the dihedral angles φ (phi) constitute values within the interval $[-90°<\phi<-40°]$; preferably the dihedral angles φ (phi) and ψ (psi) constitute values within the intervals $[-90°<\psi<-40°]$ and $[-180°<\psi<-150°$ or $-80<\$g\ c)<10$ or $100<\psi<180]$; and which positions(s) is/are not located in regions in which the enzyme is characterized by possessing α-helical or β-sheet structure. The invention also relates to nucleotide sequences encoding the novel stabilized enzymes, and expression vectors and host organisms containing the nucleotide sequences. This invention also relates to detergent compositions comprising the stabilized enzymes.

9 Claims, 17 Drawing Sheets

```
     H
     i
 SAn B         S                      A
 acc s         t                      c
 IcI m         u                      c
 III I         I                      I
    GTCGACGCATTCCGAATACGAGGCCTGATTAATGATTACATACGCCTCCGGGTAGTAGAC
   1---------+---------+---------+---------+---------+---------+ 60
    CAGCTGCGTAAGGCTTATGCTCCGGACTAATTACTAATGTATGCGGAGGCCCATCATCTG H
                         a
                         e
                         I
                         I
    CGAGCAGCCGAGCCAGTTCAGCGCCTAAAACGCCTTATACAATTAAGCAGTTAAAGAAGT
  61---------+---------+---------+---------+---------+---------+ 120
    GCTCGTCGGCTCGGTCAAGTCGCGGATTTTGCGGAATATGTTAATTCGTCAATTTCTTCA C
                                    l
                                    a
                                    I
    TAGAATCTACGCTTAAAAAGCTACTTAAAAATCGATCTCGCAGTCCCGATTCGCCTATCA
 121---------+---------+---------+---------+---------+---------+ 180
    ATCTTAGATGCGAATTTTTCGATGAATTTTTAGCTAGAGCGTCAGGGCTAAGCGGATAGT D             B                         S
           r             a                         s
           a             n                         p
           I             I                         I
    AAACCAGTTTAAATCAACTGATTAAAGGTGCCGAACGAGCTATAAATGATATAACAATAT
 181---------+---------+---------+---------+---------+---------- 240
    TTTGGTCAAATTTAGTTGACTAATTTCCACGGCTTGCTCGATATTTACTATATTGTTATA TAAAGCATTAATTAGAGCAATATCAGGCCGCGCACGAAAGGCAACTTAAAAAGCGAAAGC
 241---------+---------+---------+---------+---------+---------+ 300
    ATTTCGTAATTAATCTCGTTATAGTCCGGCGCGTGCTTTCCGTTGAATTTTTCGCTTTCG H                                        D
     a                                        r
     e                                        a
     I                                        I
    GCTCTACTAAACAGATTACTTTTGAAAAAGGCACATCAGTATTTAAAGCCCGAATCCTTA
 301---------+---------+---------+---------+---------+---------- 360
    CGAGATGATTTGTCTAATGAAAACTTTTTCCGTGTAGTCATAAATTTCGGGCTTAGGAAT
```

```
H
i
S A n         B                          S                                          A
a c c         s                          t                                          c
l c I         m                          u                                          c
III           I                          I                                          I

GTCGACGCATTCCGAATACGAGGCCTGATTAATGATTACATACGCCTCCGGGTAGTAGAC
1 ---------+---------+---------+---------+---------+---------+ 60
     CAGCTGCGTAAGGCTTATGCTCCGGACTAATTACTAATGTATGCGGAGGCCCATCATCTG
```

```
                                        H
                                        a
                                        e
                                        I
                                        I

CGAGCAGCCGAGCCAGTTCAGCGCCTAAAACGCCTTATACAATTAAGCAGTTAAAGAAGT
61  ---------+---------+---------+---------+---------+---------+ 120
      GCTCGTCGGCTCGGTCAAGTCGCGGATTTTGCGGAATATGTTAATTCGTCAATTTCTTCA
```

```
                                C
                                l
                                a
                                I

TAGAATCTACGCTTAAAAAGCTACTTAAAAATCGATCTCGCAGTCCCGATTCGCCTATCA
121  ---------+---------+---------+---------+---------+---------+ 180
       ATCTTAGATGCGAATTTTTCGATGAATTTTTAGCTAGAGCGTCAGGGCTAAGCGGATAGT
```

```
              D                          B                                          S
              r                          a                                          s
              a                          n                                          p
              I                          I                                          I

AAACCAGTTTAAATCAACTGATTAAAGGTGCCGAACGAGCTATAAATGATATAACAATAT
181 ---------+---------+---------+---------+---------+---------- 240
     TTTGGTCAAATTTAGTTGACTAATTTCCACGGCTTGCTCGATATTTACTATATTGTTATA
```

```
     TAAAGCATTAATTAGAGCAATATCAGGCCGCGCACGAAAGGCAACTTAAAAAGCGAAAGC
241 ---------+---------+---------+---------+---------+---------+ 300
     ATTTCGTAATTAATCTCGTTATAGTCCGGCGCGTGCTTTCCGTTGAATTTTTCGCTTTCG
```

```
        H                                                          D
        a                                                          r
        e                                                          a
        I                                                          I
        I

GCTCTACTAAACAGATTACTTTTGAAAAAGGCACATCAGTATTTAAAGCCCGAATCCTTA
301   ---------+---------+---------+---------+---------+---------+ 360
        CGAGATGATTTGTCTAATGAAAACTTTTTCCGTGTAGTCATAAATTTCGGGCTTAGGAAT
```

Fig. 1a

```
              H                                  B
              a                                  g
              e                                  l
              I                                  I
              I
    TTAAGCGCCGAAATCAGGCAGATAAAGCCATACAGGCAGATAGACCTCTACCTATTAAAT
361 ---------+---------+---------+---------+---------+---------+ 420
    AATTCGCGGCTTTAGTCCGTCTATTTCGGTATGTCCGTCTATCTGGAGATGGATAATTTA
              B
              s
              s
              H
              I
              I
    CGGCTTCTAGGCGCGCTCCATCTAAATGTTCTGGCTGTGGTGTACAGGGGCATAAAATTA
421 ---------+---------+---------+---------+---------+---------+ 480
    GCCGAAGATCCGCGCGAGGTAGATTTACAAGACCGACACCACATGTCCCCGTATTTTAAT
                                                         E
              C                                          c
              l                                          o
              a                                          R
              I                                          I
    CGCACTACCCGAATCGATAGAACTACTCATTTTTATATAGAAGTCAGAATTCATAGTGTT
481 ---------+---------+---------+---------+---------+---------+ 540
    GCGTGATGGGCTTAGCTATCTTGATGAGTAAAAATATATCTTCAGTCTTAAGTATCACAA
     B        D
     c        r
     l        a
     I        I
    TTGATCATTTTAAATTTTTATATGGCGGGTGGTGGGCAACTCGCTTGCGCGGGCAACTCG
541 ---------+---------+---------+---------+---------+---------+ 600
    AACTAGTAAAATTTAAAAATATACCGCCCACCACCCGTTGAGCGAACGCGCCCGTTGAGC

CTTACCGATTACGTTAGGGCTGATATTTACGTGAAAATCGTCAAGGGATGCAAGACCAAA
601 ---------+---------+---------+---------+---------+---------+ 660
    GAATGGCTAATGCAATCCCGACTATAAATGCACTTTTAGCAGTTCCCTACGTTCTGGTTT
                                    H
                                    i
                                    n
                                    c
                                    I
                                    I
    GTAGTAAAACCCCGGAAGTCAACAGCATCCAAGCCCAAGTCCTTCACGGAGAAACCCCAG
661 ---------+---------+---------+---------+---------+---------+ 720
    CATCATTTTGGGGCCTTCAGTTGTCGTAGGTTCGGGTTCAGGAAGTGCCTCTTTGGGGTC
```

Fig. 1b

```
                 CGTCCACATCACGAGCGAAGGACCACCTCTAGGCATCGGACGCACCATCCAATTAGAAGC
721--------+---------+---------+---------+---------+---------+780
                 GCAGGTGTAGTGCTCGCTTCCTGGTGGAGATCCGTAGCCTGCGTGGTAGGTTAATCTTCG
                                                                     B
                                                                     c
                                                                     l
                                                                     I

AGCAAAGCGAAACAGCCCAAGAAAAAGGTCGGCCCGTCGGCCTTTTCTGCAACGCTGATC
781--------+---------+---------+---------+---------+---------+840
                 TCGTTTCGCTTTGTCGGGTTCTTTTTCCAGCCGGGCAGCCGGAAAAGACGTTGCGACTAG
                                                                     D
                                                                     r
                                                                     a
                                                                     I

ACGGGCAGCGATCCAACCAACACCCTCCAGAGTGACTAGGGGCGGAAATTTAAAGGGATT
841--------+---------+---------+---------+---------+---------+900
                 TGCCCGTCGCTAGGTTGGTTGTGGGAGGTCTCACTGATCCCCGCCTTTAAATTTCCCTAA
                                              P         B         D
                                              s         s         r
                                              t         m         a
                                              I         I         I
                 AATTTCCACTCAACCACAAATCACAGTCGTCCCCGGTATTGTCCTGCAGAATGCAATTTA
901--------+---------+---------+---------+---------+---------+960
                 TTAAAGGTGAGTTGGTGTTTAGTGTCAGCAGGGGCCATAACAGGACGTCTTACGTTAAAT

AACTCTTCTGCGAATCGCTTGGATTCCCCGCCCCTAGTCGTAGAGCTTAAAGTATGTCCC
961--------+---------+---------+---------+---------+---------+1020
                 TTGAGAAGACGCTTAGCGAACCTAAGGGGCGGGGATCAGCATCTCGAATTTCATACAGGG

TTGTCGATGCGATGATACACAACATATAAATACTAGCAAGGGATGCCATGCTTGGAGGAT
1021-------+---------+---------+---------+---------+---------+1080
                 AACAGCTACGCTACTATGTGTTGTATATTTATGATCGTTCCCTACGGTACGAACCTCCTA
                                                                     B
                                                                     a
                                                                     m
                                                                     H
                                                                     I
                 AGCAACCGACAACATCACATCAAGCTCTCCCTTCTCTGAACAATAAACCCCACAGGGGGG
1081-------+---------+---------+---------+---------+---------+1140
                 TCGTTGGCTGTTGTAGTGTAGTTCGAGAGGGAAGAGACTTGTTATTTGGGGTGTCCCCCC
```

Fig. 1c

```
           B
           s
           p
           B1H
           a2gS                                    S   C  B
           n8ia                                    t   f  a
           I6Ac                                    y   r  l
           III                                     I   I  I
                ///
       ATCCACCATGAGGAGCTCCCTTGTGCTGTTCTTTGTCTCTGCGTGGACGGCCTTGGCCAG
1141---------+---------+---------+---------+---------+---------+1200
       TAGGTGGTACTCCTCGAGGGAACACGACAAGAAACAGAGACGCACCTGCCGGAACCGGTC

MetArgSerSerLeuValLeuPhePheValSerAlaTrpThrAlaLeuAlaSer
          ------------------pre-pro region-------------------

A
                                l
                                w
                                N
                                I
       TCCTATTCGTCGAGAGGTCTCGCAGGATCTGTTTAACCAGTTCAATCTCTTTGCACAGTA
1201---------+---------+---------+---------+---------+---------+1260
       AGGATAAGCAGCTCTCCAGAGCGTCCTAGACAAATTGGTCAAGTTAGAGAAACGTGTCAT

ProIleArgArgGluValSerGlnAspLeuPheAsnGlnPheAsnLeuPheAlaGlnTyr
       ------------||------mature lipase-------------

P              A
          P                                v              p
          s                                u              a
          t                                I              L
          I                                I              I
       TTCTGCAGCCGCATACTGCGGAAAAAACAATGATGCCCCAGCTGGTACAAACATTACGTG
1261---------+---------+---------+---------+---------+---------+1320
       AAGACGTCGGCGTATGACGCCTTTTTTGTTACTACGGGGTCGACCATGTTTGTAATGCAC
          SerAlaAlaAlaTyrCysGlyLysAsnAsnAspAlaProAlaGlyThrAsnIleThrCys-

B
       s
       p
       1H
       2g                          A
       8i                          v
       6A                          a
       II                          I
        /
       CACGGGAAATGCCTGCCCCGAGGTAGAGAAGGCGGATGCAACGTTTCTCTACTCGTTTGA
1321---------+---------+---------+---------+---------+---------+1380
       GTGCCCTTTACGGACGGGGCTCCATCTCTTCCGCCTACGTTGCAAAGAGATGAGCAAACT
       ThrGlyAsnAlaCysProGluValGluLysAlaAspAlaThrPheLeuTyrSerPheGlu-

AGACTCTGGAGTGGGCGATGTCACCGGCTTCCTTGCTCTCGACAACACGAACAAATTGAT
1381---------+---------+---------+---------+---------+---------+1440
       TCTGAGACCTCACCCGCTACAGTGGCCGAAGGAACGAGAGCTGTTGTGCTTGTTTAACTA
       AspSerGlyValGlyAspValThrGlyPheLeuAlaLeuAspAsnThrAsnLysLeuIle-
```

Fig. 1d

```
     CGTCCTCTCTTTCCGTGGCTCTCGTTCCATAGAGAACTGGATCGGGAATCTTAACTTCGA
1441 ------------------------------------------------------------+1500
     GCAGGAGAGAAAGGCACCGAGAGCAAGGTATCTCTTGACCTAGCCCTTAGAATTGAAGCT
      ValLeuSerPheArgGlySerArgSerIleGluAsnTrpIleGlyAsnLeuAsnPheAsp-

P
                              s
                              t
                              I

CTTGAAAGAAATAAATGACATTTGCTCCGGCTGCAGGGGACATGACGGCTTCACTTCGTC
1501 ------------------------------------------------------------+1560
     GAACTTTCTTTATTTACTGTAAACGAGGCCGACGTCCCCTGTACTGCCGAAGTGAAGCAG
      LeuLysGluIleAsnAspIleCysSerGlyCysArgGlyHisAspGlyPheThrSerSer-

CTGGAGGTCTGTAGCCGATACGTTAAGGCAGAAGGTGGAGGATGCTGTGAGGGAGCATCC
1561 ------------------------------------------------------------+1620
     GACCTCCAGACATCGGCTATGCAATTCCGTCTTCCACCTCCTACGACACTCCCTCGTAGG
      TrpArgSerValAlaAspThrLeuArgGlnLysValGluAspAlaValArgGluHisPro-

CGACTATCGCGTGGTGTTTACCGGACATAGCTTGGGTGGTGCATTGGCAACTGTTGCCGG
1621 ------------------------------------------------------------+1680
     GCTGATAGCGCACCACAAATGGCCTGTATCGAACCCACCACGTAACCGTTGACAACGGCC
      AspTyrArgValValPheThrGlyHisSerLeuGlyGlyAlaLeuAlaThrValAlaGly-

A
      B              E          f              A    H
      s              c          l        N     BhN  a    A
      p              o          I        d     aaa  e    v
      M              R          I        e     nIr  I    a
      I              V          I        I     III  I    I
                                                         /
     AGCAGACCTGCGTGGAAATGGGTATGATATCGACGTGTTTTCATATGGCGCCCCCCGAGT
1681 ------------------------------------------------------------+1740
     TCGTCTGGACGCACCTTTACCCATACTATAGCTGCACAAAAGTATACCGCGGGGGGCTCA
      AlaAspLeuArgGlyAsnGlyTyrAspIleAspValPheSerTyrGlyAlaProArgVal- E
                          c
                          o
                          R
                          I
     CGGAAACAGGGCTTTTGCAGAATTCCTGACCGTACAGACCGGCGGAACACTCTACCGCAT
1741 ------------------------------------------------------------+1800
     GCCTTTGTCCCGAAAACGTCTTAAGGACTGGCATGTCTGGCCGCCTTGTGAGATGGCGTA
      GlyAsnArgAlaPheAlaGluPheLeuThrValGlnThrGlyGlyThrLeuTyrArgIle-
```

Fig. 1e

```
                                      E
                                      c
                                      o
                                      R
                                      I
     TACCCACACCAATGATATTGTCCCTAGACTCCCGCCGCGCGAATTCGGTTACAGCCATTC
1801---------+---------+---------+---------+---------+---------+1860
     ATGGGTGTGGTTACTATAACAGGGATCTGAGGGCGGCGCGCTTAAGCCAATGTCGGTAAG
      ThrHisThrAsnAspIleValProArgLeuProProArgGluPheGlyTyrSerHisSer-

B                                                 E
            Ss                                                c
            ct                                                o
            aX                                                R
            II                                                V
     TAGCCCAGAGTACTGGATCAAATCTGGAACCCTTGTCCCCGTCACCCGAAACGATATCGT
1861---------+---------+---------+---------+---------+---------+1920
     ATCGGGTCTCATGACCTAGTTTAGACCTTGGGAACAGGGGCAGTGGGCTTTGCTATAGCA
      SerProGluTyrTrpIleLysSerGlyThrLeuValProValThrArgAsnAspIleVal-

B
                                                    s        E
              C                                     p        c
              l                                     M        o
              a                                     I        R
              I                                     I        V
     GAAGATAGAAGGCATCGATGCCACCGGCGGCAATAACCAGCCTAACATTCCGGATATCCC
1921---------+---------+---------+---------+---------+---------+1980
     CTTCTATCTTCCGTAGCTACGGTGGCCGCCGTTATTGGTCGGATTGTAAGGCCTATAGGG
      LysIleGluGlyIleAspAlaThrGlyGlyAsnAsnGlnProAsnIleProAspIlePro-

A
                            f
        F                   l              C    N    B
        s                   I              f    a    g
        p                   I              r    e    l
        I                   I              I    I    I
     TGCGCACCTATGGTACTTCGGGTTAATTGGGACATGTCTTTAGTGGCCGGCGCGGCTGGG
1981---------+---------+---------+---------+---------+---------+2040
     ACGCGTGGATACCATGAAGCCCAATTAACCCTGTACAGAAATCACCGGCCGCGCCGACCC
      AlaHisLeuTrpTyrPheGlyLeuIleGlyThrCysLeuEnd

B
                s
                p
              B1HB
            Aa2ggSXX
            vn8ilahb                                      A
            aI6AIcoa                                      c
            IIIIIIII                                      c
              // //                                       I
     TCCGACTCTAGCGAGCTCGAGATCTAGAGGGTGACTGACACCTGGCGGTAGACAATCAAT
2041---------+---------+---------+---------+---------+---------+2100
     AGGCTGAGATCGCTCGAGCTCTAGATCTCCCACTGACTGTGGACCGCCATCTGTTAGTTA
```

Fig. 1f

```
                                                   B
                                                   c
                                                   l
                                                   I
       CCATTTCGCTATAGTTAAAGGATGGGGATGAGGGCAATTGGTTATATGATCATGTATGTA
2101   ---------+---------+---------+---------+---------+---------+2160
       GGTAAAGCGATATCAATTTCCTACCCCTACTCCCGTTAACCAATATACTAGTACATACAT

GTGGGTGTGCATAATAGTAGTGAAATGGAAGCCAAGTCATGTGATTGTAATCGACCGACG
2161   ---------+---------+---------+---------+---------+---------+2220
       CACCCACACGTATTATCATCACTTTACCTTCGGTTCAGTACACTAACATTAGCTGGCTGC

B
       E   s
       c   p                                       N S
       o   M                                       c t
       R   I                                       o y
       V   I                                       I I
                                                     /
       GAATTGAGGATATCCGGAAATACAGACACCGTGAAAGCCATGGTCTTTCCTTCGTGTAGA
2221   ---------+---------+---------+---------+---------+---------+2280
       CTTAACTCCTATAGGCCTTTATGTCTGTGGCACTTTCGGTACCAGAAAGGAAGCACATCT

A
                     l
                     w                                       B
                     N                                       s
                     I                                       m
                                                             I
       AGACCAGACAGACAGTCCCTGATTTACCCTTGCACAAAGCACTAGAAAATTAGCATTCCA
2281   ---------+---------+---------+---------+---------+---------+2340
       TCTGGTCTGTCTGTCAGGGACTAAATGGGAACGTGTTTCGTGATCTTTTAATCGTAAGGT

B
                                                                s
                                                                p
                        E                                       B1H
                        c                       N               a2gS
                        o                       s               n8ia
                        R                       i               I6Ac
                        V                       I               III
                                                                 ///
       TCCTTCTCTGCTTGCTCTGCTGATATCACTGTCATTCAATGCATAGCCATGAGCTCATCT
2341   ---------+---------+---------+---------+---------+---------+2400
       AGGAAGAGACGAACGAGACGACTATAGTGACAGTAAGTTACGTATCGGTACTCGAGTAGA

TAGATCCAAGCACGTAATTCCATAGCCGAGGTCCACAGTGGAGCAGCAACATTCCCCATC
2401   ---------+---------+---------+---------+---------+---------+2460
       ATCTAGGTTCGTGCATTAAGGTATCGGCTCCAGGTGTCACCTCGTCGTTGTAAGGGGTAG
```

Fig. 1g

```
                    D
                    r
                    a
                    I
                    I
                    I
       ATTGCTTTCCCCAGGGGCCTCCCAACGACTAAATCAAGAGTATATCTCTACCGTCCAATA
2461   ---------+---------+---------+---------+---------+---------+  2520
       TAACGAAAGGGGTCCCCGGAGGGTTGCTGATTTAGTTCTCATATAGAGATGGCAGGTTAT

D P
                                        r p
                                        a u
                                        I M
                                        I I
                                          /
       GATCGTCTTCGCTTCAAAATCTTTGACAATTCCAAGAGGGTCCCCATCCATCAAACCCAG
2521   ---------+---------+---------+---------+---------+---------+  2580
       CTAGCAGAAGCGAAGTTTTAGAAACTGTTAAGGTTCTCCCAGGGGTAGGTAGTTTGGGTC

N
                        s
                        i
                        I
       TTCAATAATAGCCGAGATGCATGGTGGAGTCAATTAGGCAGTATTGCTGGAATGTCGGGC
2581   ---------+---------+---------+---------+---------+---------+  2640
       AAGTTATTATCGGCTCTACGTACCACCTCAGTTAATCCGTCATAACGACCTTACAGCCCG

A X S                 C
               v m m                 f
               a a a                 r
               I I I                 I
                 /
       CAGTTGGCCCGGGTGGTCATTGGCCGCCTGTGATGCCATCTGCCACTAAATCCGATCATT
2641   ---------+---------+---------+---------+---------+---------+  2700
       GTCAACCGGGCCCACCAGTAACCGGCGGACACTACGGTAGACGGTGATTTAGGCTAGTAA

A
                    B                                 h
                    g                                 a
                    l                                 I
                    I                                 I
       GATCCACCGCCCACGAGGCGCGTCTTTGCTTTTTGCGCGGCGTCCAGGTTCAACTCTCTC
2701   ---------+---------+---------+---------+---------+---------+  2760
       CTAGGTGGCGGGTGCTCCGCGCAGAAACGAAAAACGCGCCGCAGGTCCAAGTTGAGAGAG

E       E
           X     c   C   c
           b     o   l   o
           a     R   a   R
           I     V   I   I
       GCTCTAGATATCGATGAATTC
2761   ---------+----------  2781
       CGAGATCTATAGCTACTTAAG
```

Fig. 1h

Enzymes that do cut:

| | | | | | |
|---|---|---|---|---|---|
| AccI | AflIII | AhaII | AlwNI | ApaLI | AvaI | BalI |
| BanI | BanII | BclI | BglI | BglII | BsmI | Bsp1286I |
| BspMII | BssHII | BstXI | CfrI | ClaI | DraI | DraII |
| EcoRV | FspI | HaeII | HgiAI | HincII | NaeI | NarI |
| NdeI | NsiI | PpuMI | PstI | PvuII | SacI | SalI |
| SmaI | SspI | StuI | StyI | XbaI | XhoI | XmaI |

| | | |
|---|---|---|
| | | BamHI |
| | | BspMI |
| | | EcoRI |
| | | NcoI |
| | | ScaI |

Enzymes that do not cut:

| | | | | | |
|---|---|---|---|---|---|
| AatII | AflII | ApaI | AvrII | BspHI | BstEII | DraIII | EcoNI |
| HindIII | HpaI | KpnI | MluI | NheI | NotI | NruI | PflMI |
| PvuI | RsrII | SacII | SfiI | SnaBI | SpeI | SphI | Tth111I |

Fig. 1i

```
ATGAGGAGCTCCCTTGTGCTGTTCTTTGTCTCTGCGTGGACGGCCTTGGCCAGT
MetArgSerSerLeuValLeuPhePheValSerAlaTrpThrAlaLeuAlaSer
------------------pre-pro region------------------

CCTATTCGTCGAGAGGTCTCGCAGGATCTGTTTAACCAGTTCAATCTCTTTGCACAGTAT
ProIleArgArgGluValSerGlnAspLeuPheAsnGlnPheAsnLeuPheAlaGlnTyr
-----------||-----mature lipase-------------

TCTGCAGCCGCATACTGCGGAAAAAACAATGATGCCCCAGCTGGTACAAACATTACGTGC
SerAlaAlaAlaTyrCysGlyLysAsnAsnAspAlaProAlaGlyThrAsnIleThrCys

ACGGGAAATGCCTGCCCCGAGGTAGAGAAGGCGGATGCAACGTTTCTCTACTCGTTTGAA
ThrGlyAsnAlaCysProGluValGluLysAlaAspAlaThrPheLeuTyrSerPheGlu

GACTCTGGAGTGGGCGATGTCACCGGCTTCCTTGCTCTCGACAACACGAACAAATTGATC
AspSerGlyValGlyAspValThrGlyPheLeuAlaLeuAspAsnThrAsnLysLeuIle

GTCCTCTCTTTCCGTGGCTCTCGTTCCATAGAGAACTGGATCGGGAATCTTAACTTCGAC
ValLeuSerPheArgGlySerArgSerIleGluAsnTrpIleGlyAsnLeuAsnPheAsp

TTGAAAGAAATAAATGACATTTGCTCCGGCTGCAGGGGACATGACGGCTTCACTTCGTCC
LeuLysGluIleAsnAspIleCysSerGlyCysArgGlyHisAspGlyPheThrSerSer

TGGAGGTCTGTAGCCGATACGTTAAGGCAGAAGGTGGAGGATGCTGTGAGGGAGCATCCC
TrpArgSerValAlaAspThrLeuArgGlnLysValGluAspAlaValArgGluHisPro

GACTATCGCGTGGTGTTTACCGGACATAGCTTGGGTGGTGCATTGGCAACTGTTGCCGGA
AspTyrArgValValPheThrGlyHisSerLeuGlyGlyAlaLeuAlaThrValAlaGly

GCAGACCTGCGTGGAAATGGGTATGATATCGACGTGTTTTCATATGGCGCCCCCGAGTC
AlaAspLeuArgGlyAsnGlyTyrAspIleAspValPheSerTyrGlyAlaProArgVal
```

Fig. 5a

```
GGAAACAGGGCTTTTGCAGAATTCCTGACCGTACAGACCGGCGGAACACTCTACCGCATT
GlyAsnArgAlaPheAlaGluPheLeuThrValGlnThrGlyGlyThrLeuTyrArgIle

ACCCACACCAATGATATTGTCCCTAGACTCCCGCCGCGCGAATTCGGTTACAGCCATTCT
ThrHisThrAsnAspIleValProArgLeuProProArgGluPheGlyTyrSerHisSer

AGCCCAGAGTACTGGATCAAATCTGGAACCCTTGTCCCCGTCACCCGAAACGATATCGTG
SerProGluTyrTrpIleLysSerGlyThrLeuValProValThrArgAsnAspIleVal

AAGATAGAAGGCATCGATGCCACCGGCGGCAATAACCAGCCTAACATTCCGGATATCCCT
LysIleGluGlyIleAspAlaThrGlyGlyAsnAsnGlnProAsnIleProAspIlePro

GCGCACCTATGGTACTTCGGGTTAATTGGGACATGTCTTTAGTGGCCGGCGCGGCTGGG
AlaHisLeuTrpTyrPheGlyLeuIleGlyThrCysLeuEnd
```

Fig. 5b

```
GGATCCAAG ATG CGT TCC TCC CCC CTC CTC CCG TCC GCC GTT GTG GCC    48
          Met Arg Ser Ser Pro Leu Leu Pro Ser Ala Val Val Ala
          -21 -20              -15                  -10

GCC CTG CCG GTG TTG GCC CTT GCC GCT GAT GGC AGG TCC ACC CGC TAC   96
Ala Leu Pro Val Leu Ala Leu Ala Ala Asp Gly Arg Ser Thr Arg Tyr
         -5                   1                   5

TGG GAC TGC TGC AAG CCT TCG TGC GGC TGG GCC AAG AAG GCT CCC GTG  144
Trp Asp Cys Cys Lys Pro Ser Cys Gly Trp Ala Lys Lys Ala Pro Val
        10                  15                  20

AAC CAG CCT GTC TTT TCC TGC AAC GCC AAC TTC CAG CGT ATC ACG GAC  192
Asn Gln Pro Val Phe Ser Cys Asn Ala Asn Phe Gln Arg Ile Thr Asp
    25                  30                  35                  40

TTC GAC GCC AAG TCC GGC TGC GAG CCG GGC GGT GTC GCC TAC TCG TGC  240
Phe Asp Ala Lys Ser Gly Cys Glu Pro Gly Gly Val Ala Tyr Ser Cys
            45                  50                  55

GCC GAC CAG ACC CCA TGG GCT GTG AAC GAC GAC TTC GCG CTC GGT TTT  288
Ala Asp Gln Thr Pro Trp Ala Val Asn Asp Asp Phe Ala Leu Gly Phe
                60                  65                  70

GCT GCC ACC TCT ATT GCC GGC AGC AAT GAG GCG GGC TGG TGC TGC GCC  336
Ala Ala Thr Ser Ile Ala Gly Ser Asn Glu Ala Gly Trp Cys Cys Ala
        75                  80                  85

TGC TAC GAG CTC ACC TTC ACA TCC GGT CCT GTT GCT GGC AAG AAG ATG  384
Cys Tyr Glu Leu Thr Phe Thr Ser Gly Pro Val Ala Gly Lys Lys Met
    90                  95                  100

GTC GTC CAG TCC ACC AGC ACT GGC GGT GAT CTT GGC AGC AAC CAC TTC  432
Val Val Gln Ser Thr Ser Thr Gly Gly Asp Leu Gly Ser Asn His Phe
105                 110                 115                 120

GAT CTC AAC ATC CCC GGC GGC GGC GTC GGC ATC TTC GAC GGA TGC ACT  480
Asp Leu Asn Ile Pro Gly Gly Gly Val Gly Ile Phe Asp Gly Cys Thr
            125                 130                 135
```

Fig. 6a

```
CCC CAG TTC GGC GGT CTG CCC GGC CAG CGC TAC GGC GGC ATC TCG TCC   528
Pro Gln Phe Gly Gly Leu Pro Gly Gln Arg Tyr Gly Gly Ile Ser Ser
            140                 145                 150

CGC AAC GAG TGC GAT CGG TTC CCC GAC GCC CTC AAG CCC GGC TGC TAC   576
Arg Asn Glu Cys Asp Arg Phe Pro Asp Ala Leu Lys Pro Gly Cys Tyr
            155                 160                 165

TGG CGC TTC GAC TGG TTC AAG AAC GCC GAC AAT CCG AGC TTC AGC TTC   624
Trp Arg Phe Asp Trp Phe Lys Asn Ala Asp Asn Pro Ser Phe Ser Phe
            170                 175                 180

CGT CAG GTC CAG TGC CCA GCC GAG CTC GTC GCT CGC ACC GGA TGC CGC   672
Arg Gln Val Gln Cys Pro Ala Glu Leu Val Ala Arg Thr Gly Cys Arg
185                 190                 195                 200

CGC AAC GAC GAC GGC AAC TTC CCT GCC GTC CAG ATC CCC TCC AGC AGC   720
Arg Asn Asp Asp Gly Asn Phe Pro Ala Val Gln Ile Pro Ser Ser Ser
                    205                 210                 215

ACC AGC TCT CCG GTC AAC CAG CCT ACC AGC ACC AGC ACC ACG TCC ACC   768
Thr Ser Ser Pro Val Asn Gln Pro Thr Ser Thr Ser Thr Thr Ser Thr
                220                 225                 230

TCC ACC ACC TCG AGC CCG CCA GTC CAG CCT ACG ACT CCC AGC GGC TGC   816
Ser Thr Thr Ser Ser Pro Pro Val Gln Pro Thr Thr Pro Ser Gly Cys
            235                 240                 245

ACT GCT GAG AGG TGG GCT CAG TGC GGC GGC AAT GGC TGG AGC GGC TGC   864
Thr Ala Glu Arg Trp Ala Gln Cys Gly Gly Asn Gly Trp Ser Gly Cys
            250                 255                 260

ACC ACC TGC GTC GCT GGC AGC ACT TGC ACG AAG ATT AAT GAC TGG TAC   912
Thr Thr Cys Val Ala Gly Ser Thr Cys Thr Lys Ile Asn Asp Trp Tyr
265                 270                 275                 280

CAT CAG TGC CTG TAGACGCAGG GCAGCTTGAG GGCCTTACTG GTGGCCGCAA       964
His Gln Cys Leu
            285

CGAAATGACA CTCCCAATCA CTGTATTAGT TCTTGTACAT AATTTCGTCA           1014

TCCCTCCAGG GATTGTCACA TAAATGCAAT GAGGAACAAT GAGTAC               1060
```

Fig. 6b

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 2781 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1148..2020

(ix) FEATURE:
      (A) NAME/KEY: sig_peptide
      (B) LOCATION: 1148..1213

(ix) FEATURE:
      (A) NAME/KEY: mat_peptide
      (B) LOCATION: 1214..2020

(xi) SEQUENCE DESCRIPTION: SEQ ID NO:1:

```
GTCGACGCAT TCCGAATACG AGGCCTGATT AATGATTACA TACGCCTCCG GGTAGTAGAC      60

CGAGCAGCCG AGCCAGTTCA GCGCCTAAAA CGCCTTATAC AATTAAGCAG TTAAAGAAGT     120
```

-continued

```
TAGAATCTAC GCTTAAAAAG CTACTTAAAA ATCGATCTCG CAGTCCCGAT TCGCCTATCA     180

AAACCAGTTT AAATCAACTG ATTAAAGGTG CCGAACGAGC TATAAATGAT ATAACAATAT     240

TAAAGCATTA ATTAGAGCAA TATCAGGCCG CGCACGAAAG GCAACTTAAA AAGCGAAAGC     300

GCTCTACTAA ACAGATTACT TTTGAAAAAG GCACATCAGT ATTTAAAGCC CGAATCCTTA     360

TTAAGCGCCG AAATCAGGCA GATAAAGCCA TACAGGCAGA TAGACCTCTA CCTATTAAAT     420

CGGCTTCTAG GCGCGCTCCA TCTAAATGTT CTGGCTGTGG TGTACAGGGG CATAAAATTA     480

CGCACTACCC GAATCGATAG AACTACTCAT TTTTATATAG AAGTCAGAAT TCATAGTGTT     540

TTGATCATTT TAAATTTTTA TATGGCGGGT GGTGGGCAAC TCGCTTGCGC GGGCAACTCG     600

CTTACCGATT ACGTTAGGGC TGATATTTAC GTGAAAATCG TCAAGGGATG CAAGACCAAA     660

GTAGTAAAAC CCCGGAAGTC AACAGCATCC AAGCCCAAGT CCTTCACGGA GAAACCCCAG     720

CGTCCACATC ACGAGCGAAG GACCACCTCT AGGCATCGGA CGCACCATCC AATTAGAAGC     780

AGCAAAGCGA AACAGCCCAA GAAAAGGTC GGCCCGTCGG CCTTTTCTGC AACGCTGATC     840

ACGGGCAGCG ATCCAACCAA CACCCTCCAG AGTGACTAGG GGCGGAAATT TAAAGGGATT     900

AATTTCCACT CAACCACAAA TCACAGTCGT CCCCGGTATT GTCCTGCAGA ATGCAATTTA     960

AACTCTTCTG CGAATCGCTT GGATTCCCCG CCCCTAGTCG TAGAGCTTAA AGTATGTCCC    1020

TTGTCGATGC GATGATACAC AACATATAAA TACTAGCAAG GGATGCCATG CTTGGAGGAT    1080

AGCAACCGAC AACATCACAT CAAGCTCTCC CTTCTCTGAA CAATAAACCC CACAGGGGGG    1140

ATCCACC ATG AGG AGC TCC CTT GTG CTG TTC TTT GTC TCT GCG TGG ACG     1189
        Met Arg Ser Ser Leu Val Leu Phe Phe Val Ser Ala Trp Thr
        -22     -20             -15             -10

GCC TTG GCC AGT CCT ATT CGT CGA GAG GTC TCG CAG GAT CTG TTT AAC    1237
Ala Leu Ala Ser Pro Ile Arg Arg Glu Val Ser Gln Asp Leu Phe Asn
            -5              1               5

CAG TTC AAT CTC TTT GCA CAG TAT TCT GCA GCC GCA TAC TGC GGA AAA    1285
Gln Phe Asn Leu Phe Ala Gln Tyr Ser Ala Ala Ala Tyr Cys Gly Lys
        10              15              20

AAC AAT GAT GCC CCA GCT GGT ACA AAC ATT ACG TGC ACG GGA AAT GCC    1333
Asn Asn Asp Ala Pro Ala Gly Thr Asn Ile Thr Cys Thr Gly Asn Ala
25              30              35              40

TGC CCC GAG GTA GAG AAG GCG GAT GCA ACG TTT CTC TAC TCG TTT GAA    1381
Cys Pro Glu Val Glu Lys Ala Asp Ala Thr Phe Leu Tyr Ser Phe Glu
                45              50              55

GAC TCT GGA GTG GGC GAT GTC ACC GGC TTC CTT GCT CTC GAC AAC ACG    1429
Asp Ser Gly Val Gly Asp Val Thr Gly Phe Leu Ala Leu Asp Asn Thr
            60              65              70

AAC AAA TTG ATC GTC CTC TCT TTC CGT GGC TCT CGT TCC ATA GAG AAC    1477
Asn Lys Leu Ile Val Leu Ser Phe Arg Gly Ser Arg Ser Ile Glu Asn
        75              80              85

TGG ATC GGG AAT CTT AAC TTC GAC TTG AAA GAA ATA AAT GAC ATT TGC    1525
Trp Ile Gly Asn Leu Asn Phe Asp Leu Lys Glu Ile Asn Asp Ile Cys
    90              95              100

TCC GGC TGC AGG GGA CAT GAC GGC TTC ACT TCG TCC TGG AGG TCT GTA    1573
Ser Gly Cys Arg Gly His Asp Gly Phe Thr Ser Ser Trp Arg Ser Val
105             110             115             120

GCC GAT ACG TTA AGG CAG AAG GTG GAG GAT GCT GTG AGG GAG CAT CCC    1621
Ala Asp Thr Leu Arg Gln Lys Val Glu Asp Ala Val Arg Glu His Pro
                125             130             135

GAC TAT CGC GTG GTG TTT ACC GGA CAT AGC TTG GGT GGT GCA TTG GCA    1669
Asp Tyr Arg Val Val Phe Thr Gly His Ser Leu Gly Gly Ala Leu Ala
            140             145             150
```

```
ACT GTT GCC GGA GCA GAC CTG CGT GGA AAT GGG TAT GAT ATC GAC GTG          1717
Thr Val Ala Gly Ala Asp Leu Arg Gly Asn Gly Tyr Asp Ile Asp Val
        155                 160                 165

TTT TCA TAT GGC GCC CCC CGA GTC GGA AAC AGG GCT TTT GCA GAA TTC          1765
Phe Ser Tyr Gly Ala Pro Arg Val Gly Asn Arg Ala Phe Ala Glu Phe
170                 175                 180

CTG ACC GTA CAG ACC GGC GGA ACA CTC TAC CGC ATT ACC CAC ACC AAT          1813
Leu Thr Val Gln Thr Gly Gly Thr Leu Tyr Arg Ile Thr His Thr Asn
185                 190                 195                 200

GAT ATT GTC CCT AGA CTC CCG CCG CGC GAA TTC GGT TAC AGC CAT TCT          1861
Asp Ile Val Pro Arg Leu Pro Pro Arg Glu Phe Gly Tyr Ser His Ser
            205                 210                 215

AGC CCA GAG TAC TGG ATC AAA TCT GGA ACC CTT GTC CCC GTC ACC CGA          1909
Ser Pro Glu Tyr Trp Ile Lys Ser Gly Thr Leu Val Pro Val Thr Arg
        220                 225                 230

AAC GAT ATC GTG AAG ATA GAA GGC ATC GAT GCC ACC GGC GGT AAT AAC          1957
Asn Asp Ile Val Lys Ile Glu Gly Ile Asp Ala Thr Gly Gly Asn Asn
                235                 240                 245

CAG CCT AAC ATT CCG GAT ATC CCT GCG CAC CTA TGG TAC TTC GGG TTA          2005
Gln Pro Asn Ile Pro Asp Ile Pro Ala His Leu Trp Tyr Phe Gly Leu
        250                 255                 260

ATT GGG ACA TGT CTT TAGTGGCCGG CGCGGCTGGG TCCGACTCTA GCGAGCTCGA          2060
Ile Gly Thr Cys Leu
265

GATCTAGAGG GTGACTGACA CCTGGCGGTA GACAATCAAT CCATTTCGCT ATAGTTAAAG        2120

GATGGGGATG AGGGCAATTG GTTATATGAT CATGTATGTA GTGGGTGTGC ATAATAGTAG        2180

TGAAATGGAA GCCAAGTCAT GTGATTGTAA TCGACCGACG GAATTGAGGA TATCCGGAAA        2240

TACAGACACC GTGAAAGCCA TGGTCTTTCC TTCGTGTAGA AGACCAGACA GACAGTCCCT        2300

GATTTACCCT TGCACAAAGC ACTAGAAAAT TAGCATTCCA TCCTTCTCTG CTTGCTCTGC        2360

TGATATCACT GTCATTCAAT GCATAGCCAT GAGCTCATCT TAGATCCAAG CACGTAATTC        2420

CATAGCCGAG GTCCACAGTG GAGCAGCAAC ATTCCCCATC ATTGCTTTCC CCAGGGGCCT        2480

CCCAACGACT AAATCAAGAG TATATCTCTA CCGTCCAATA GATCGTCTTC GCTTCAAAAT        2540

CTTTGACAAT TCCAAGAGGG TCCCCATCCA TCAAACCCAG TTCAATAATA GCCGAGATGC        2600

ATGGTGGAGT CAATTAGGCA GTATTGCTGG AATGTCGGGC CAGTTGGCCC GGGTGGTCAT        2660

TGGCCGCCTG TGATGCCATC TGCCACTAAA TCCGATCATT GATCCACCGC CCACGAGGCG        2720

CGTCTTTGCT TTTTGCGCGG CGTCCAGGTT CAACTCTCTC GCTCTAGATA TCGATGAATT        2780

C                                                                        2781

(2) INFORMATION FOR SEQ ID NO:2:

(i) SEQUENCE CHARACTERISTICS:
        (A) LENGTH: 291 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Ser Ser Leu Val Leu Phe Phe Val Ser Ala Trp Thr Ala Leu
-22         -20                 -15                 -10

Ala Ser Pro Ile Arg Arg Glu Val Ser Gln Asp Leu Phe Asn Gln Phe
        -5                  1                   5                   10

Asn Leu Phe Ala Gln Tyr Ser Ala Ala Ala Tyr Cys Gly Lys Asn Asn
                15                  20                  25
```

| | | | | | | | | | | | |
|---|---|---|---|---|---|---|---|---|---|---|---|
| Asp | Ala | Pro | Ala | Gly | Thr | Asn | Ile | Thr | Cys | Thr | Gly | Asn | Ala | Cys | Pro |
| | | | 30 | | | | 35 | | | | 40 | |

Asp Ala Pro Ala Gly Thr Asn Ile Thr Cys Thr Gly Asn Ala Cys Pro
            30                35                40

Glu Val Glu Lys Ala Asp Ala Thr Phe Leu Tyr Ser Phe Glu Asp Ser
        45                50                55

Gly Val Gly Asp Val Thr Gly Phe Leu Ala Leu Asp Asn Thr Asn Lys
    60                65                70

Leu Ile Val Leu Ser Phe Arg Gly Ser Arg Ser Ile Glu Asn Trp Ile
75              80                85                            90

Gly Asn Leu Asn Phe Asp Leu Lys Glu Ile Asn Asp Ile Cys Ser Gly
                95                100               105

Cys Arg Gly His Asp Gly Phe Thr Ser Ser Trp Arg Ser Val Ala Asp
            110               115               120

Thr Leu Arg Gln Lys Val Glu Asp Ala Val Arg Glu His Pro Asp Tyr
        125               130               135

Arg Val Val Phe Thr Gly His Ser Leu Gly Gly Ala Leu Ala Thr Val
    140               145               150

Ala Gly Ala Asp Leu Arg Gly Asn Gly Tyr Asp Ile Asp Val Phe Ser
155             160               165               170

Tyr Gly Ala Pro Arg Val Gly Asn Arg Ala Phe Ala Glu Phe Leu Thr
            175               180               185

Val Gln Thr Gly Gly Thr Leu Tyr Arg Ile Thr His Thr Asn Asp Ile
        190               195               200

Val Pro Arg Leu Pro Pro Arg Glu Phe Gly Tyr Ser His Ser Ser Pro
        205               210               215

Glu Tyr Trp Ile Lys Ser Gly Thr Leu Val Pro Val Thr Arg Asn Asp
        220               225               230

Ile Val Lys Ile Glu Gly Ile Asp Ala Thr Gly Gly Asn Asn Gln Pro
235             240               245               250

Asn Ile Pro Asp Ile Pro Ala His Leu Trp Tyr Phe Gly Leu Ile Gly
            255               260               265

Thr Cys Leu (2) INFORMATION FOR SEQ ID NO:3:

(i) SEQUENCE CHARACTERISTICS:
        (A) LENGTH: 1060 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 10..924

(ix) FEATURE:
        (A) NAME/KEY: sig_peptide
        (B) LOCATION: 10..72

(ix) FEATURE:
        (A) NAME/KEY: mat_peptide
        (B) LOCATION: 73..924

(xi) SEQUENCE DESCRIPTION: SEQ ID NO:3:

```
GGATCCAAG ATG CGT TCC TCC CCC CTC CTC CCG TCC GCC GTT GTG GCC             48
          Met Arg Ser Ser Pro Leu Leu Pro Ser Ala Val Val Ala
          -21 -20              -15                 -10

GCC CTG CCG GTG TTG GCC CTT GCC GCT GAT GGC AGG TCC ACC CGC TAC           96
Ala Leu Pro Val Leu Ala Leu Ala Ala Asp Gly Arg Ser Thr Arg Tyr
         -5                   1               5
```

| | | |
|---|---|---|
| TGG GAC TGC TGC AAG CCT TCG TGC GGC TGG GCC AAG AAG GCT CCC GTG<br>Trp Asp Cys Cys Lys Pro Ser Cys Gly Trp Ala Lys Lys Ala Pro Val<br>10                      15                    20 | | 144 |
| AAC CAG CCT GTC TTT TCC TGC AAC GCC AAC TTC CAG CGT ATC ACG GAC<br>Asn Gln Pro Val Phe Ser Cys Asn Ala Asn Phe Gln Arg Ile Thr Asp<br>25                      30                    35                    40 | | 192 |
| TTC GAC GCC AAG TCC GGC TGC GAG CCG GGC GGT GTC GCC TAC TCG TGC<br>Phe Asp Ala Lys Ser Gly Cys Glu Pro Gly Gly Val Ala Tyr Ser Cys<br>                  45                    50                    55 | | 240 |
| GCC GAC CAG ACC CCA TGG GCT GTG AAC GAC GAC TTC GCG CTC GGT TTT<br>Ala Asp Gln Thr Pro Trp Ala Val Asn Asp Asp Phe Ala Leu Gly Phe<br>                      60                    65                    70 | | 288 |
| GCT GCC ACC TCT ATT GCC GGC AGC AAT GAG GCG GGC TGG TGC TGC GCC<br>Ala Ala Thr Ser Ile Ala Gly Ser Asn Glu Ala Gly Trp Cys Cys Ala<br>        75                    80                    85 | | 336 |
| TGC TAC GAG CTC ACC TTC ACA TCC GGT CCT GTT GCT GGC AAG AAG ATG<br>Cys Tyr Glu Leu Thr Phe Thr Ser Gly Pro Val Ala Gly Lys Lys Met<br>        90                    95                    100 | | 384 |
| GTC GTC CAG TCC ACC AGC ACT GGC GGT GAT CTT GGC AGC AAC CAC TTC<br>Val Val Gln Ser Thr Ser Thr Gly Gly Asp Leu Gly Ser Asn His Phe<br>105                   110                    115                  120 | | 432 |
| GAT CTC AAC ATC CCC GGC GGC GTC GGC ATC TTC GAC GGA TGC ACT<br>Asp Leu Asn Ile Pro Gly Gly Val Gly Ile Phe Asp Gly Cys Thr<br>                  125                    130                  135 | | 480 |
| CCC CAG TTC GGC GGT CTG CCC GGC CAG CGC TAC GGC GGC ATC TCG TCC<br>Pro Gln Phe Gly Gly Leu Pro Gly Gln Arg Tyr Gly Gly Ile Ser Ser<br>              140                    145                  150 | | 528 |
| CGC AAC GAG TGC GAT CGG TTC CCC GAC GCC CTC AAG CCC GGC TGC TAC<br>Arg Asn Glu Cys Asp Arg Phe Pro Asp Ala Leu Lys Pro Gly Cys Tyr<br>                  155                    160                  165 | | 576 |
| TGG CGC TTC GAC TGG TTC AAG AAC GCC GAC AAT CCG AGC TTC AGC TTC<br>Trp Arg Phe Asp Trp Phe Lys Asn Ala Asp Asn Pro Ser Phe Ser Phe<br>170                   175                    180 | | 624 |
| CGT CAG GTC CAG TGC CCA GCC GAG CTC GTC GCT CGC ACC GGA TGC CGC<br>Arg Gln Val Gln Cys Pro Ala Glu Leu Val Ala Arg Thr Gly Cys Arg<br>185                   190                    195                  200 | | 672 |
| CGC AAC GAC GAC GGC AAC TTC CCT GCC GTC CAG ATC CCC TCC AGC AGC<br>Arg Asn Asp Asp Gly Asn Phe Pro Ala Val Gln Ile Pro Ser Ser Ser<br>                  205                    210                  215 | | 720 |
| ACC AGC TCT CCG GTC AAC CAG CCT ACC AGC ACC AGC ACC ACG TCC ACC<br>Thr Ser Ser Pro Val Asn Gln Pro Thr Ser Thr Ser Thr Thr Ser Thr<br>              220                    225                  230 | | 768 |
| TCC ACC ACC TCG AGC CCG CCA GTC CAG CCT ACG ACT CCC AGC GGC TGC<br>Ser Thr Thr Ser Ser Pro Pro Val Gln Pro Thr Thr Pro Ser Gly Cys<br>        235                    240                    245 | | 816 |
| ACT GCT GAG AGG TGG GCT CAG TGC GGC GGC AAT GGC TGG AGC GGC TGC<br>Thr Ala Glu Arg Trp Ala Gln Cys Gly Gly Asn Gly Trp Ser Gly Cys<br>250                   255                    260 | | 864 |
| ACC ACC TGC GTC GCT GGC AGC ACT TGC ACG AAG ATT AAT GAC TGG TAC<br>Thr Thr Cys Val Ala Gly Ser Thr Cys Thr Lys Ile Asn Asp Trp Tyr<br>265                   270                    275                  280 | | 912 |
| CAT CAG TGC CTG TAGACGCAGG GCAGCTTGAG GGCCTTACTG GTGGCCGCAA<br>His Gln Cys Leu | | 964 |
| CGAAATGACA CTCCCAATCA CTGTATTAGT TCTTGTACAT AATTTCGTCA TCCCTCCAGG | | 1024 |
| GATTGTCACA TAAATGCAAT GAGGAACAAT GAGTAC | | 1060 |

(2) INFORMATION FOR SEQ ID NO:4:

(i) SEQUENCE CHARACTERISTICS:
        (A) LENGTH: 305 amino acids
        (B) TYPE: amino acid (D) TOPOLOGY: linear (ii) MOLECULE TYPE: protein (xi) SEQUENCE DESCRIPTION: SEQ ID NO:4:

| Met | Arg | Ser | Ser | Pro | Leu | Leu | Pro | Ser | Ala | Val | Val | Ala | Ala | Leu | Pro |
|---|---|---|---|---|---|---|---|---|---|---|---|---|---|---|---|
| -21 | -20 | | | | -15 | | | | -10 | | | | | | |

| Val | Leu | Ala | Leu | Ala | Ala | Asp | Gly | Arg | Ser | Thr | Arg | Tyr | Trp | Asp | Cys |
|---|---|---|---|---|---|---|---|---|---|---|---|---|---|---|---|
| -5 | | | | | 1 | | | | 5 | | | | | 10 | |

Cys Lys Pro Ser Cys Gly Trp Ala Lys Lys Ala Pro Val Asn Gln Pro
              15                  20                  25

Val Phe Ser Cys Asn Ala Asn Phe Gln Arg Ile Thr Asp Phe Asp Ala
          30                  35                  40

Lys Ser Gly Cys Glu Pro Gly Gly Val Ala Tyr Ser Cys Ala Asp Gln
      45                  50                  55

Thr Pro Trp Ala Val Asn Asp Asp Phe Ala Leu Gly Phe Ala Ala Thr
  60                  65                  70                  75

Ser Ile Ala Gly Ser Asn Glu Ala Gly Trp Cys Cys Ala Cys Tyr Glu
              80                  85                  90

Leu Thr Phe Thr Ser Gly Pro Val Ala Gly Lys Lys Met Val Val Gln
              95                  100                 105

Ser Thr Ser Thr Gly Gly Asp Leu Gly Ser Asn His Phe Asp Leu Asn
          110                 115                 120

Ile Pro Gly Gly Gly Val Gly Ile Phe Asp Gly Cys Thr Pro Gln Phe
      125                 130                 135

Gly Gly Leu Pro Gly Gln Arg Tyr Gly Gly Ile Ser Ser Arg Asn Glu
140                 145                 150                 155

Cys Asp Arg Phe Pro Asp Ala Leu Lys Pro Gly Cys Tyr Trp Arg Phe
              160                 165                 170

Asp Trp Phe Lys Asn Ala Asp Asn Pro Ser Phe Ser Phe Arg Gln Val
          175                 180                 185

Gln Cys Pro Ala Glu Leu Val Ala Arg Thr Gly Cys Arg Arg Asn Asp
      190                 195                 200

Asp Gly Asn Phe Pro Ala Val Gln Ile Pro Ser Ser Ser Thr Ser Ser
      205                 210                 215

Pro Val Asn Gln Pro Thr Ser Thr Ser Thr Ser Thr Ser Thr Ser Thr
220                 225                 230                 235

Ser Ser Pro Pro Val Gln Pro Thr Thr Pro Ser Gly Cys Thr Ala Glu
              240                 245                 250

Arg Trp Ala Gln Cys Gly Gly Asn Gly Trp Ser Gly Cys Thr Thr Cys
              255                 260                 265

Val Ala Gly Ser Thr Cys Thr Lys Ile Asn Asp Trp Tyr His Gln Cys
          270                 275                 280

Leu (2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GGGGACAAGG GTTGGAGATT TGATCCA                                27

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGTCATCCAG TCACTGAGAC CCTCTACCTA TTAAATCGGC          40

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CCATGGCTTT CACGGTGTCT          20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGTCATCCAG TCACTGAGAC          20

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GACAAGGGTT CCTGGTTTGA TCCAGTA          27

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GCCGGTGGCA TCTGGGCCTT CTATCTT          27

(2) INFORMATION FOR SEQ ID NO:11:

(i) SEQUENCE CHARACTERISTICS:
        (A) LENGTH: 25 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TATTGCCGCC GGGGGCATCG ATGCC                                               25

STABILIZED ENZYMES

TECHNICAL FIELD

This invention relates to novel stabilized enzymes. More specifically the invention relates to novel stabilized enzymes, in which a naturally occurring amino acid residue (other than proline) has been substituted with a proline residue at one or more positions; at which position(s) the dihedral angels φ (phi) constitute values within the interval [−90°<φ−40°]; preferably the dihedral angels φ (phi) and ψ (psi) constitute values within the intervals [−90°<φ<−40°] and [−180°<ψ<−150°] or −80<ψ<10 or λ100<ψ<180]; and which position(s) is/are not located in regions in which the enzyme is characterized by possessing α-helical or β-sheet structure.

The invention also relates to nucleotide sequences encoding the novel stabilized enzymes, and expression vectors and host organisms containing the nucleotide sequences. The invention also relates to detergent compositions comprising the stabilized enzymes.

BACKGROUND ART

The Structure of Proteins

Enzymes are globular proteins and quiet compact due to the considerable amount of folding of the long polypeptide chain. The polypeptide chain essentially consists of the "backbone" and its "side-groups". As the peptide bond is planar, only rotations around the $C_\alpha$—N axis and the $C_\alpha$—C' axis are permitted. Rotation around the $C_\alpha$—N bond of the peptide backbone is denoted by the torsion angle φ (phi), rotation around the $C_\alpha$—C' bond by ψ (psi) [vide, e.g. Creighton, T. E. (1984), Proteins; W. H. Freeman and Company, New York]. The choice of the values of these angles of rotation is made by assigning the maximum value of +180° (which is identical to +180°) to the maximally extended chain. In the fully extended polypeptide chain, the $N_1$ $C_\alpha$ and C' atoms are all "trans" to each other. In the "cis" configuration, the angles φ and ψ are assigned the value of 0°. Rotation from this position around the bonds, so that the atoms viewed behind the rotated bond move "counterclockwise", are assigned negative values by definition, those "clockwise" are assigned positive values. Thus, the values of the torsion angles lie within the range −180° to +180°.

Since the $C_{60}$-atoms are the swivel point for the chain, the side-groups (R-groups) associated with the $C_{60}$-atoms become extremely important with respect to the conformation of the molecule.

The term "conformation" defines the participation of the secondary and tertiary structures of the polypeptide chains in moulding the overall structure of a protein. The correct conformation of a protein is of prime importance to the specific structure of a protein and contributes greatly to the unique catalytic properties (i.e. activity and specificity) of enzymes and their stability.

The amino acids of polypeptides can be divided into four general groups: nonpolar, uncharged polar, and negatively or positively charged polar amino acids. A protein molecule, when submerged in its aqueous environment in which it normally occurs, tends to expose a maximum number of its polar side-groups to the surrounding environment, while a majority of its nonpolar sidegroups are oriented internally. Orientation of the side-groups in this manner leads to a stabilization of protein conformation.

Proteins, thus, exist in a dynamic equilibrium between a folded and ordered state, and an unfolded and disordered state. This equilibrium in part reflects the short range interactions among the different segments of the polypeptide chain, which tends to stabilize the overall structure of proteins. Thermodynamic forces simultaneously tend to promote randomization of the unfolding molecule.

A way to engineer stabilized proteins is to reduce the extend of unfolding by decreasing the flexibility of the polypeptide backbone, and simultaneously decreasing the entropy of the unfolded chain. So far only few attempts have been made to implement this rationale in the development of novel stabilized enzymes.

A genera principle of increasing protein thermostability has been provided [Suzuki, Y. (1989); Proc. Japan Acad.; 65 Ser. B]. In this article Suzuki states that the thermostability of a globular protein can be enhanced cumulatively to a great extent by increasing the frequency of proline occurrence at the second site of β-turns without significant alterations in the secondary and tertiary structures as well as in the catalytic function of enzymes. The principle is based on various facts and findings, among these the fact the proline residues show a strong tendency to occur preferentially at the second site of β-turns [Levitt, M (1978); Biochemistry; 17 4277–4285; and Chou, P. Y. & Fasman, G. D. (1977); J. Mol. Biol.; 115 135–175]. The principle is restricted to insertion of proline into the second site of 62-turns in proteins, no other sites are mentioned.

International Patent Publication WO 08/01520 (Cetus Corporation, USA) provides a method for increasing the stability of a protein by decreasing the configurational entropy of unfolding the protein. The method is applied on a *Streptomyces rubiqinosus* xylose isomerase, and it involves substitution of an amino acid with proline, or replacement of glycine with alanine, at predicted substitution sites.

It is an object of this invention to provide novel enzymes having improved stability.

SUMMARY OF THE INVENTION

The present invention provides novel stabilized enzymes, in which a naturally occurring amino acid residue (other than proline) has been substituted with a proline residue at one or more positions, at which position(s) the dihedral angles φ (phi) constitute values within the interval [−90°<φ<−40°], preferably the dihedral angles φ (phi) constitute values within the intervals [−90°<φ<−40°] and [−180°ψ<−150° or −80<ψ<10 or 100<ψ<180], and which position(s) is/are not located in regions in which the enzyme is characterized by possessing α-helical or β-sheet structure.

In another aspect, the invention relates to nucleotide sequences encoding novel stabilized enzymes, expression vectors comprising these nucleotide sequences, and host organisms containing these expression vectors.

Enzymes

In the context of this invention, an enzyme may be any enzyme apart from proteases, such as e.g. a lipase, a cellulase, a peroxidase, a xylanase, or an amylase.

Amino Acids

As abbreviations for amino acids the following symbols are used:

| | | | | |
|---|---|---|---|---|
| A | = | Ala | = | Alanine |
| C | = | Cys | = | Cysteine |
| D | = | Asp | = | Aspartic acid |
| E | = | Glu | = | Glutamic acid |
| F | = | Phe | = | Phenylalanine |
| G | = | Gly | = | Glycine |
| H | = | His | = | Histidine |
| I | = | Ile | = | Isoleucine |
| K | = | Lys | = | Lysine |
| L | = | Leu | = | Leucine |
| M | = | Met | = | Methionine |
| N | = | Asn | = | Asparagine |
| P | = | Pro | = | Proline |
| Q | = | Gln | = | Glutamine |
| R | = | Arg | = | Arginine |
| S | = | Ser | = | Serine |
| T | = | Thr | = | Threonine |
| V | = | Val | = | Valine |
| W | = | Trp | = | Tryptophan |
| Y | = | Tyr | = | Tyrosine |
| B | = | Asx | = | Asp (D) or Asn (N) |
| Z | = | Glx | = | Glu (E) or Gln (Q) |

X = an arbitrary amino acid
* = deletion or absent amino acid

Enzyme Variants

A stabilized enzyme of this invention is an enzyme variant or mutated enzyme. By an enzyme variant or mutated enzyme is meant an enzyme obtainable by alteration of a DNA nucleotide sequence of the parent gene or its derivatives. The enzyme variant or mutated enzyme may be expressed and produced when the DNA nucleotide sequence encoding the enzyme is inserted into a suitable vector in a suitable host organism. The host organism is not necessarily identical to the organism from which the parent gene originated.

Amino Acid Numbering

In the context of this invention, a specific numbering of amino acid residue positions in enzyme is employed.

In describing the various enzyme variants produced or contemplated according to the invention, the following nomenclatures were adapted for ease of reference:

[Original amino acid; Position; Substituted amino acid]

According to this, the substitution of glycine with proline in position 225 is designated as G225P.

If a substitution, e.g. G225P, is made by mutation in e.g. *Humicola lanuginosa* lipase, the product is designated "*Humicola lanuginosa*/G225P lipase".

Enzymatic Activity.

In the context of this invention, the enzymatic activity of lipases is expressed in Lipase units. A Lipase Unit (LU) is the amount of enzyme which under standard conditions, i.e., 30.0° C.; pH 7.0; tributyrine substrate, liberates 1 $\mu$mol titrable butyric acid per minute. A folder AF 95/5 describing this analytical method is available upon request to Novo Nordisk A/S, Denmark, which folder is hereby included by reference.

In the context of this invention, the enzymatic activity of cellulases is expressed in Novo Cellulase units (NCU). One unit is defined as the amount of enzyme which, under standard conditions (i.e. at pH 4.8; 0.1 M acetate buffer; 10 g/l Hercules CMC type 7 LFD as substrate; an incubation temp. of 40.0° C.; an incubation time of 20 min; and an enzyme concentration of approximately 0.041 NCU/ml) forms an amount of reducing carbohydrates equivalent to 1 $\mu$mol glucose per minute. A folder AF 1987.2/1 describing this analytical method is available upon request to Novo Nordisk A/S, Denmark, which folder is hereby included by reference.

BRIEF DESCRIPTION OF DRAWINGS

The present invention is further illustrated by reference to the accompanying drawings, in which:

FIG. 1 (sheets 1/17–9/17) shows the nucleotide sequence (SEQ ID NO:1) expression cassette of the Humicola lanuginosa lipase;

FIG. 5 (sheets 13/17–14/17) shows the amino acid sequence (and a corresponding DNA nucleotide sequence) (SEQ ID NO:1)

FIG. 6 (sheets 15/17–16/17) shows the amino acid sequence (SEQ ID NO:4) Humicola insolens cellulase obtained according to International Patent Application WO 91/17243.

DETAILED DISCLOSURE OF THE INVENTION

Figure 2:
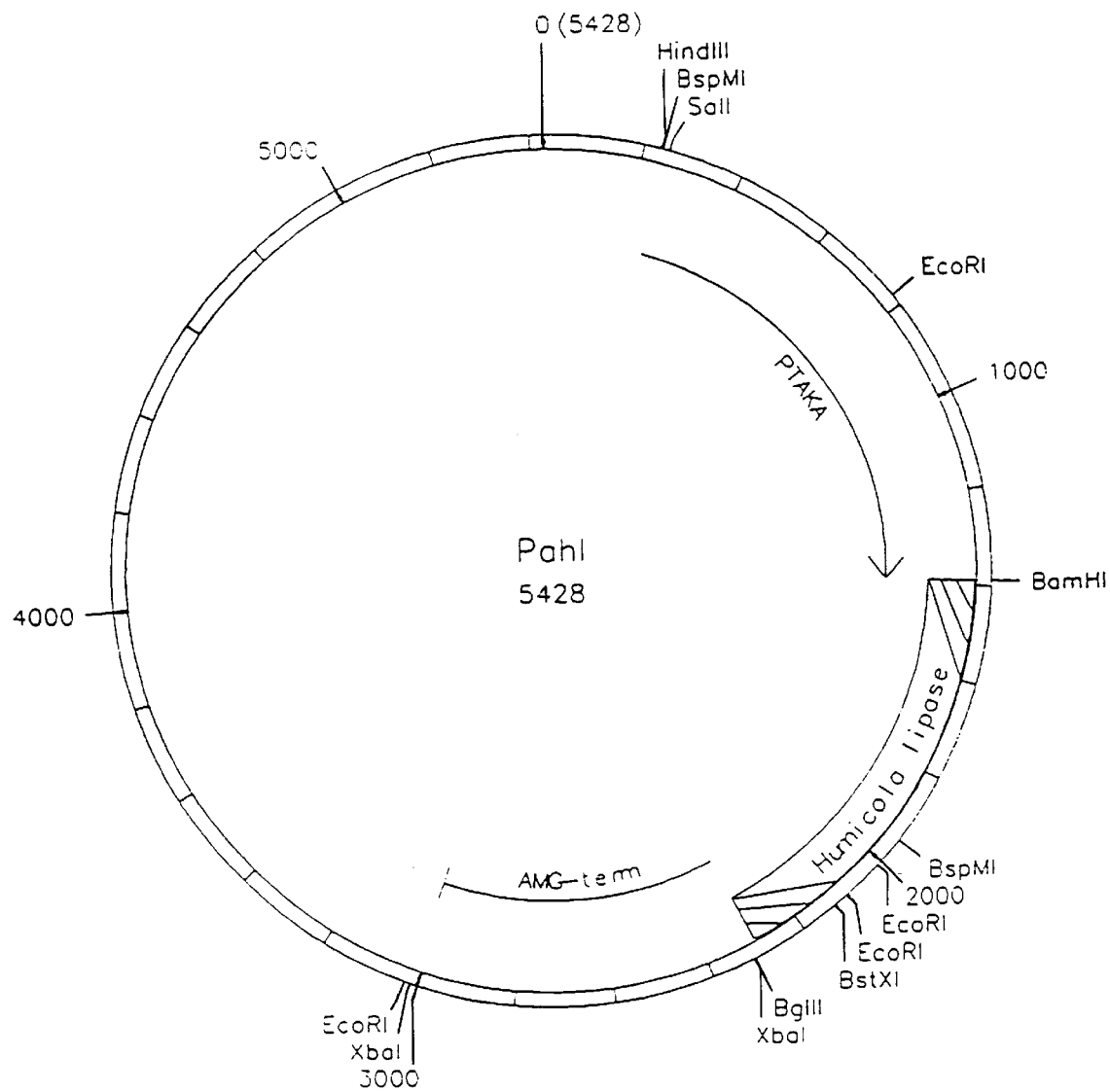
FIG. 2 shows the restriction map of plasmid pAHL.

The present invention provides novel stabilized enzymes in which a naturally occurring amino acid residue (other than proline) has been substituted with a proline residue at one or more positions, at which position(s) the dihedral angles $\phi$ (phi) constitute values in the interval $[-90°<\phi<-40°]$, preferably the dihedral angles $\phi$ (phi) and $\psi$ (psi) constitute values in the intervals $[-90<\phi<-40°]$ and $[-180°-<\psi 150°$ or $-80 <\psi<10$ or $100<\psi<180]$, and which position(s) is/are not located in regions, in which the enzyme is characterized by possessing $\alpha$-helical or $\beta$-sheet structure.

In the context of this invention, a stabilized enzyme of the invention is an enzyme variant or mutated enzyme, being functionally equivalent or having structural features similar to a naturally occurring enzyme, and in which enzyme a naturally occurring amino acid residue (other than proline) has been substituted with a proline residue at one or more positions, at which position(s) the dihedral angles $\phi$ (phi) constitute values within the intervals $[-90°<\phi<-40°]$, preferably the dihedral angles $\phi$ (phi) and $\psi$ (psi) constitute values within the intervals $[-90°<\phi<-40°]$ and $[-180°<\psi<-150°$ or $-80<\psi<$ or $100<\psi<180]$, and which position(s) is/are not located in regions in which the enzyme is characterized by possessing $\alpha$-helical or $\beta$-sheet structure.

Moreover, in the context of this invention, a stabilized enzyme is an enzyme having improved stability, e.g. in respect to thermal stability, storage stability, etc., when compared to the parent enzyme.

Defining Secondary Structure of Proteins

The stabilized enzymes of the invention may be obtained by subjecting the enzyme in question to analysis for secondary structure, identifying residues in the enzyme having dihedral angles $\phi$ (phi) confined to the interval $[-90°<\phi<-40°]$, preferably having dihedral angles $\phi$ (phi) and $\psi$ (psi)

confined to the intervals [−90°−<φ<−40°] and [−180°<ψ<−150° or −80<ψ<10 or 100<ψ<180], excluding residues located in regions in which the enzyme is characterized by possessing α-helical or β-sheet structure, if a proline residue is not already at the identified position(s), substitution of the naturally occurring amino acid residue with a proline residue at the identified position(s), preferably by site directed mutagenesis applied on a gene encoding the enzyme in question, and gene expression by insertion of the gene encoding the stabilized enzyme in a suitable host organism, followed by cultivation of said host organism in a suitable nutrient medium, and recovery of the desired enzyme.

This method of obtaining stabilized enzymes includes subjecting the enzyme in question to analysis for secondary structure. In one way to perform such analysis the atomic structure of the enzyme has to be elucidated. The atomic structure may be determined by X-ray diffraction techniques. X-ray diffraction techniques are described by e.g. Hendrickson [Hendrickson, W. A. (1987); X-ray diffraction; in Protein Engineering (Ed; Oxender, D. L. and Fox, C. F.), ch. 1; Alan R. Liss, Inc.] and Creighton [Creighton, T. E.; supra; ch. 6].

The crystal structure of a *Rhizomucor miehei* lipase has been deduced [vide Brady l., Brzozwski A. M., Derewenda Z. S., Dodson E., Dodson G., Tolley S., Turkenburg J. P., Christiansen L., Huge-Jensen B., Norskov L. Thim L. & Menge U. (1990); "A serine protease triad forms the catalytic centre of a triacylglycerol lipase"; Nature, Vol. 343 6260 767–770], and the coordinates have been deposited and are available from the Brookhaven Protein Data Bank [Bernstein et al. (1977); J. Mol. Bio. 112 535–542].

When the atomic structure has been determined, it is possible to compute dihedral angles from the atomic coordinates. Moreover, it is possible to assign secondary structure elements. The secondary structure elements are defined on the basis of hydrogen bindings. Cooperative secondary structure is recognized as repeats of the elementary hydrogen-bonding patterns "turn" and "bridge". Repeating turns are "helixes", repeating bridges are "ladders", connected ladders are "sheets".

Analysis for secondary structure elements requires a computerized compilation of structure assignments and geometrical features extracted from atomic coordinates. The conventional method to elucidate the secondary structure of a protein, based on its atomic coordinates, is described by Kabsch and Sander [Kabach, W. and Sander, C. (1983); Biopolymers, 22 2577–2637]. In this article an algorithm for extracting structural features from the atomic coordinates by a pattern-recognition process is provided. First, H-bonds are identified based on electrostatic interactions between pairs of H-bonding groups. Next, the patterns of H-bonding are used to define secondary structure elements such as turns (T), bends (S), bridges (B), helices, (G,H,I), β-ladders (E) and β-sheets (E).

A computer program DSSP (Define Secondary Structure of Proteins), enabling the computation of Kabsch & Sander files and written in standard PASCAL, is available from the Protein Data Bank, Chemistry Dept., Brookhaven National laboratory, Upton, N.Y. 11973.

Analysis for secondary structure and calculation of the dihedral angles may also be carried out by other methods, e.g. by model building [vide e.g. Sutcliffe, Haneef, Carney and Blundell (1987); Protein Engineering, 1 (5) 377–384].

After the dihedral angles φ (phi) and ψ (psi) for the amino acids have been calculated, based on the atomic structure in the crystalline enzyme, it is possible to select position(s) which has/have dihedral phi and psi angles favourable for substitution with a proline residue. The aliphatic side chain of proline residues is bonded covalently to the nitrogen atom of the peptide group. The resulting cyclic five-membered ring consequently imposes a rigid constraint on the rotation about the $N—C_{60}$ bond of the peptide backbone and simultaneously prevents the formation of hydrogen bonding to the backbone N-atom. For these structural reasons, prolines are generally not compatible with α-helical and β-sheet secondary conformations. Due to the same rotational constraint about the $C_{60}—N$ bond, and due to the requirement that neighbouring amino acids in the chain are not disturbed, the magnitudes of the dihedral angles phi and psi (and in particular phi) are confined to limited intervals for proline residues in polypeptides. The dihedral angles for proline residues in polypeptides are almost exclusively within the intervals [−90°<φ<−40°], preferably the intervals [−90°<φ<−40°] and [−180°<ψ<−150° or −80<ψ<10 or 100<ψ<180]. In this context, both cis- and trans-proline residues are considered.

A proline residue may already occur at one or more positions pointed out by the procedure described above, and then a substitution is, of course, irrelevant. Otherwise, the method includes substitution of the naturally occurring amino acid residue with a proline residue.

When performing this method on a Humicola lanuginosa lipase, obtained as described in European Patent Application No. 305,216, the positions cited in Table 1 are revealed. When performing this method on a *Rhizomucor insolens* cellulase, obtained as described in International Patent Application WO 91/17243, the positions cited in Table 2 are revealed.

Certainly it is not to be expected that a substitution into proline at every of the predicted positions would bring out improved stability of the enzyme. At some of the positions revealed by the method, a substitution of a naturally occurring amino acid residue into a proline residue may cause destabilisation due to unpredictable factors, such as loss of essential flexibility, loss of H-bond possibilities, unpredictable sterical hindrance, etc. Such "critical sites" are not always to be foreseen.

However, it is to be expected that the stabilizing (or destabilizing) effects of individual substitutions are additive [vide e.g. Well, J. A. (1990); Biochemistry; 29 (37) 8510–8517].

Preferred Enzymes

Preferably, an enzyme of the invention is a stabilized lipase, a stabilized cellulase, a stabilized peroxidase, a stabilized xylanase, or a stabilized amylase.

In one aspect an enzyme of the invention is a stabilized lipase, the lipase being obtainable from a member of the genera *Humicola, Rhizomucor, Candida,* or *Pseudomonas.*

In a specific embodiment of the invention, the enzyme is a stabilized lipase, the lipase being obtainable from a strain of *Humicola lanuginosa, Rhizomucor miehei, Candida antarctica,* or *Pseudomonas cepacia.* Lipases obtainable from *Humicola* are described in e.g. European Patent Application No. 305,216 and International patent Application WO 89/01969. Preferably, the lipase is a stabilized *Humicola lanuginosa* lipase, the lipase being obtained as described in European Patent Application No. 305,216.

In another specific embodiment of the invention, the enzyme is a stabilized lipase, the lipase being obtainable from a member of the genus *Humicola,* which stabilized lipase comprises a substitution into a proline residue at one or more of the positions listed in Table 1, or positions analogous hereto. Preferably, the enzyme is stabilized lipase, the lipase being obtainable from a strain of *Humicola lanuginosa*.

In yet another specific embodiment, an enzyme of the invention is a stabilized lipase, the lipase being obtainable from a member of the genus *Humicola*, which stabilized lipase comprises one or more of the following substitutions: A28P, G61P, N101P, S105P, D111P, D165P, R209P, S224P, G225P, T226P, R232P, N233P, I241P, (according to the amino acide sequence presented in FIG. 5 (SEQ ID NO:2) or at positions analogous hereto. Preferably, the enzyme is a stabilized lipase, the lipase being obtainable from a strain of *Humicola lanuginosa*.

In a more specific aspect, an enzyme of the invention is *Humicola lanuginosa*/G2225P lipase or *Humicola langinosa*T244P lipase.

TABLE 1

Proline Mutants Proposed in *Humicola lanuginosa* Lipase Based on phi and psi Angles.
Criteria −90° < phi < −40°;
Neither part of an alpha helix nor a beta sheet structure.

| AA numbers | phi angle | psi angle | Amino acid | Structure | Mutant & Comments |
|---|---|---|---|---|---|
| 19 | −57 | −22 | A | T | |
| 20 | −59 | −39 | A | T | |
| 21 | −62 | −42 | Y | T | |
| 23 | −65 | 175 | G | S | |
| 28 | −84 | −103 | A | S | |
| 43 | −72 | −23 | E | T | |
| 44 | −41 | −52 | V | T | |
| 45 | −44 | −48 | E | T | |
| 46 | −86 | 33 | K | T | |
| 48 | −81 | 82 | D | | |
| 61 | −88 | −105 | G | T | |
| 71 | −68 | 0 | N | T | |
| 83 | −66 | 155 | S | | |
| 84 | −83 | 8 | R | S | |
| 101 | −64 | 127 | N | T | |
| 103 | −89 | −24 | I | T | |
| 105 | −86 | −79 | S | S | |
| 111 | −68 | 172 | D | T | |
| 160 | −80 | 174 | R | T | |
| 165 | −74 | 129 | D | | |
| 173 | −83 | 142 | A | | |
| 175 | −76 | 145 | R | | |
| 178 | −81 | −160 | N | | |
| 203 | −85 | 164 | V | T | |
| 213 | −85 | 148 | Y | | |
| 216 | −74 | 167 | S | S | |
| 223 | −58 | −22 | K | | |
| 224 | −83 | 159 | S | S | |
| 225 | −70 | −178 | G | | |
| 226 | −77 | 138 | T | T | |
| 232 | −45 | −24 | R | T | |
| 234 | −89 | 9 | D | S | |
| 241 | −63 | 134 | I | T | |
| 244 | −84 | 140 | T | T | |
| 247 | −54 | −27 | N | S | |
| 255 | −78 | −34 | I | S | |
| 257 | −79 | −23 | A | T | |
| 258 | −69 | −13 | H | T | |

In another aspect an enzyme of the invention is a stabilized cellulase, the cellulase being obtainable from a member of the genera *Rhizomucor*. In a specific embodiment an enzyme of the invention is a stabilized cellulase being obtainable from a strain of *Rhizomucor miehei*. Cellulases obtainable from *Rhizomucor miehei* are described in e.g. International Patent Application WO 91/17243.

In another specific embodiment of the invention, the enzyme is a stabilized *Rhizomucor miehei* cellulase, which stabilized cellulase comprises a substitution into a proline residue at one or more of the positions listed in Table 2, or positions analogous hereto.

In yet another specific embodiment, an enzyme of the invention the enzyme is a stabilized *Rhizomucor miehei* cellulase, which stabilized cellulase comprises a substitution into a proline residue at one or more of the following positions: A33P, A78P, I131P, A162P, or at positions analogous hereto.

TABLE 2

Proline Mutants Proposed in *Rhizomucor miehei* Cellulase Based on phi and psi Angles.
Criteria −90° < phi < −40°;
Neither part of an alpha helix nor a beta sheet structure.

| AA numbers | phi angle | psi angle | Amino acid | Structure | Mutant & Comments |
|---|---|---|---|---|---|
| 19 | −68 | | A | | |
| 25 | −42 | | N | | |
| 28 | −62 | | V | | |
| 29 | −64 | | F | | |
| 32 | −78 | | N | | |
| 33 | −64 | | A | | |
| 34 | −84 | | N | | |
| 37 | −66 | | R | | |
| 39 | −89 | | T | | |
| 40 | −82 | | D | | |
| 41 | −73 | | F | | |
| 42 | −95 | | D | | |
| 43 | −61 | | A | | |
| 44 | −58 | | K | | |
| 45 | −62 | | S | | |
| 46 | −66 | | G | | |
| 51 | −80 | | G | | |
| 55 | −69 | | S | | |
| 57 | −70 | | A | | |
| 58 | −86 | | D | | |
| 66 | −75 | | D | | |
| 78 | −52 | | A | | |
| 27 | −75 | | G | | |
| 129 | −70 | | V | | |
| 131 | −78 | | I | | |
| 146 | −53 | | R | | |
| 150 | −78 | | I | | |
| 161 | −61 | | D | | |
| 162 | −64 | | A | | |
| 177 | −76 | | A | | |
| 181 | −84 | | S | | |
| 188 | −61 | | Q | | |
| 189 | | | C | | |
| 201 | −75 | | R | | |
| 202 | −68 | | N | | |
| 204 | −55 | | D | | |
| 205 | −77 | | G | | |

The Effect of Prolinstabilization

The thermostability of purified lipase variants has been tested by a differential scanning calorimetry (DSC) method, and by activity determination at elevated temperatures (vide Example 3 for experimental data). The result of this experiment is shown in Table 3, below, and in FIG. 7.

TABLE 3

Stabilization relative to *Humicola lanuginosa* Lipase

| Variant | Relative Stabilization Δ DSC |
|---|---|
| *Humicola lanuginosa*/S224P | −6.0° C. |
| *Humicola lanuginosa*/G225P | 2.0° C. |
| *Humicola lanuginosa*/I241P | −6.2° C. |

It appears from Table 3 that 3 of the variants constructed possess significantly improved thermostability, and 2 of the variants posses significantly decreased thermostability, when compared to the wild-type enzyme. These results clearly demonstrate that although a rationale exists for stabilization by introduction of proline residues into a protein by the Phi-Psi-Concept described in this specification, no conclusion as to the stabilizing effect of the individual variants are predictable.

Recombinantly Produced Enzymes

In the past, numerous processes have been developed for the production of polypeptides or proteins by means of the recombinant DNA technology. Mostly used for this purpose are *E. coli, acillus subtilis, Saccharomyces cerevisiae* and different *Aspergillus* strains, e.g. *A. oryzae* and *A. niger.* Especially the *Aspergillii* are attractive candidates as host microorganism for recombinant DNA vectors being well-characterized and widely used microorganisms for the commercial production of enzymes. In *Aspergillus oryzae*, methods have been developed for transformation of the organism, and production of several enzymes, among these the *Humicola lanuginosa* and *Rhizomucor miehei* lipases (vide e.g. European Patent Application Nos. 238,023 and 305,216, and International Patent Application No. WO 89/01969), and the *Humicola insolens* and *Fusarium oxysporium* cellulases (vide e.g. International Patent Application WO 91/17243), has also been demonstrated, which publications are hereby included by reference.

Expression of Polypeptides Biosynthetically

Upon transformation of an organism where the intention is production of a polypeptide or a protein, a DNA sequence is introduced into the organism. The sequence contains the coding region of the gene of interest flanked by transcription/translation start signals and transcription/translation termination signals. The coding region contains units of three base pairs, called codons, which upon translation of the transcribed gene are translated into amino acids, which again are assembled to give the polypeptide of interest.

Introducing Mutations in polypeptides

By changing one or more specific codons in the coding region and transforming the host microorganism with these new coding regions, new polypetides can be produce, which differ from the original polypeptide by one or more amino acids. Such alternations can be introduced by means of a technique generally known as "site-directed in vitro mutagenesis". A number of methods have been published. An early method is described by Zoller & Smith (1984); DNA 3 (6) 479–488, and involves use of the single-stranded M13 bacteriophage. A preferred method using PCR (polymerase chain reaction) is described by Nelson & Long (1989); Analytical Biochemistry, 180, 140–151. It involves a 3-step generation of a PCR fragment containing the desired mutation by using a chemically synthesized DNA oligonucleotide as one of the primers in the PCR reactions. From the PCR-generated fragment, a DNA fragment carrying the mutation can be isolated by cleavage with restriction enzymes and re-inserted into the expression plasmid. A third mutagenesis method takes advantage of restriction sites in the DNA coding region. By digesting the DNA with restriction enzymes at sites flanking the mutagenesis target, sythesizing a new fragment synthetically containing the desired mutation and cloning this new fragment between the restriction sites, a mutant coding region can be constructed.

All methods are generally applicable to investigations in the field called protein engineering which deals with the development of polypeptides with new or altered characteristics.

Transformation and expression may be accomplished by methods known in the art, e.g. as described in European Patent Application No. 305,216, which specification is hereby included by reference.

The microorganisms able to produce a stabilized enzyme of this invention can be cultivated by conventional fermentation methods in a nutrient medium containing assimilable carbon and nitrogen together with other essential nutrients, the medium being composed in accordance with the principles of the known art. Purification and recovery of the stabilized enzyme may also be conducted in accordance with methods known per se.

Nucleotide Sequences, Expression Vectors and Microorganisms

This invention also relates to DNA nucleotide sequences encoding a stabilized enzyme of the invention. The stabilized enzyme may be expressed and produced when DNA nucleotide sequence encoding this enzyme is inserted into a suitable vector in a suitable host organism. The host organism is not necessarily identical to the organism from which the parent gene originated. The construction of the mutated genes, vectors and mutant and transformed microorganisms may be carried out by an appropriate recombinant DNA technique, known in the art.

The invention also relates to expression vectors and host organisms containing a DNA nucleotide encoding a stabilized enzyme of this invention.

Detergent Compositions

The present invention also comprises the use of stabilized enzymes of the invention in cleaning and detergent compositions and such compositions comprising one or more stabilized enzymes of the invention.

The detergent composition of the invention may comprise one or more surfactants, which may be of a anionic, non-ionic, cat-ionic, amphoteric or zwitterionic type, or a mixture of these. Typical examples of anionic surfactants are linear alkyl benzene sulfonates (LAS), alkyl sulfates (AS), alpha olefin sulfonates (AOS), alcohol ethoxy sulfates (AES) and alkali metal salts of natural fatty acids. Examples on non-ionic surfactants are alkyl polyethylene glycol ethers, nonylphenol polyethylene glycol ethers, fatty acids esters of sucrose and glucose, and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in J. Falbe [Falbe J.; Surfactants in Consumer Products. Theory, Technology and Application, Springer Verlag 1987, vide in particular the section entitled "Frame formulations for liquid/powder heavy-duty detergents"].

It is at present contemplated that the detergent composition of the invention may contain a protease preparation in an amount corresponding to 0.0005–0.5 CPU of the proteolytic enzyme per litre of washing liquor. Generally, detergent compositions are used in dosages within the range of 0.3 to 15 g detergent per litre wash liquor.

The detergent compositions of the invention can be formulated in any convenient form, such as powders, liquids, etc.

The enzymes of the invention may be included in a detergent composition by adding separate additives containing one or more enzymes, or by adding a combined additive comprising all of these enzymes.

The additive of the invention, i.e. a separated additive or a combined additive, can be formulated e.g. as granulates, liquids, slurries, etc. Preferred detergent additive formulations are non-dusting granulates, liquids, in particular stabilized liquids, slurries, or protected enzymes.

Dust free granulates may be produced according to e.g. GB Patent No. 1,362,365 or U.S. Pat. No. 4,106,991, and may optionally be coated by methods known in the art. The detergent enzymes may be mixed before or after granulation.

Liquid enzyme preparations may, for instance, be stabilized by adding a polyol such as e.g. propylene glycol, a sugar or sugar alcohol, lactic acid or boric acid, according to established methods. Other enzyme stabilizers are well known in the art.

Protected enzymes may be prepared according to the method disclosed in EP Patent Application No. 238,216.

The invention is further illustrated in the following examples, which are not intended to be in any way limiting to the scope of the invention as claimed.

EXAMPLE 1

Construction of a Plasmid Expressing the G225P Variant of *Humicola lanuginosa* Lipase The expression plasmid used in this specification is identical to p960, described in European Patent Application No. 305,216, except for minor modifications just 3' to the lipase coding regions. The modifications were made the following way:

p960 was digested with NruI and BamHI restriction enzymes. Between these two sites the BamHI/NheI fragment from plasmid pBR322, in which the NheI fragment was filled in with Klenow polymerase, was cloned, thereby creating plasmid pAOI, which contained unique BamHI and HheI sites, Between these unique sites BamHI/XbaI fragments for p960 were cloned to give pAHL.

Figure 3:
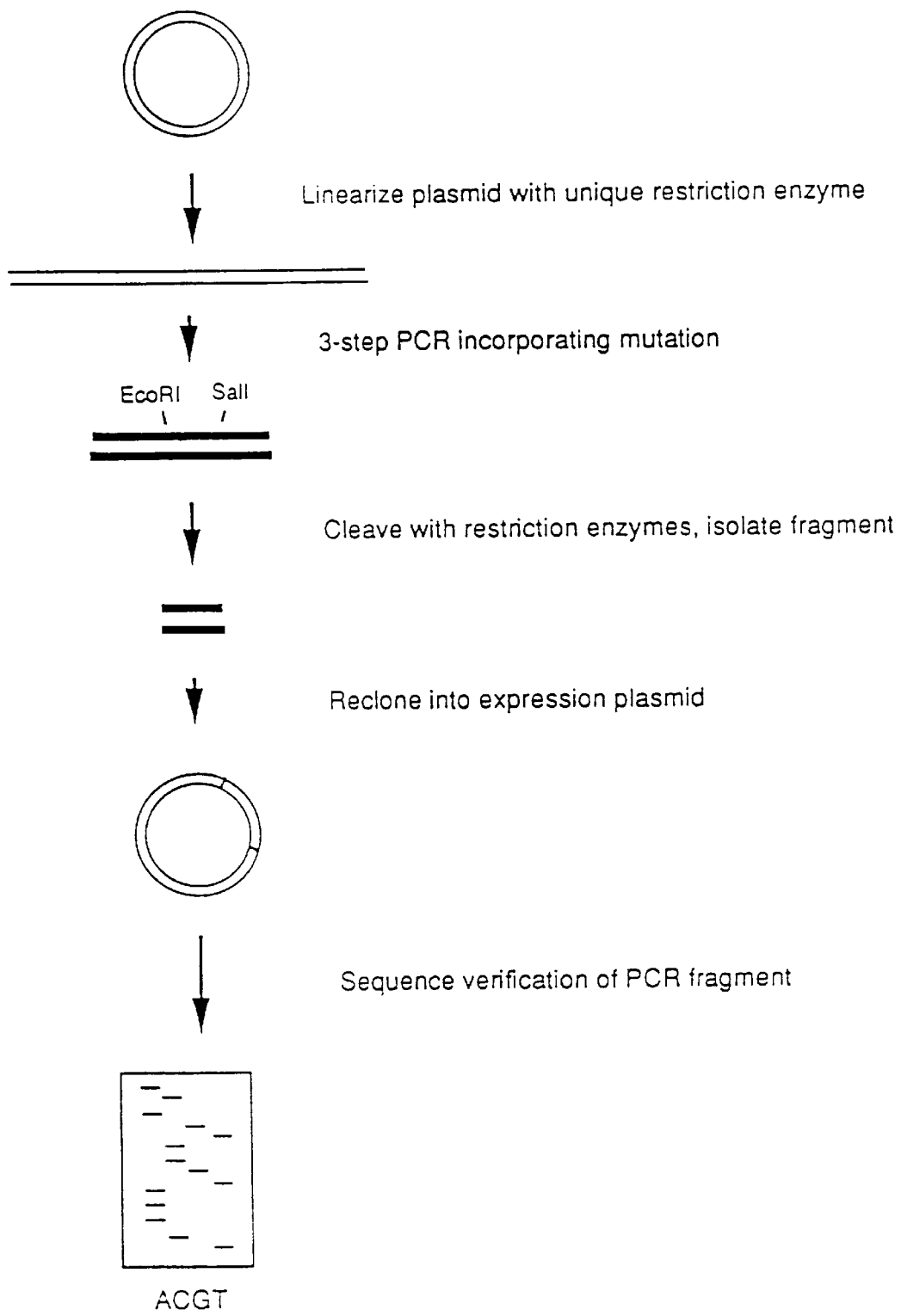
FIGS. 3–4 shows the PCR technique for producing *Humincola* lipase variants.

The sequence of the SAII/EcoRI fragment comprising the expression cassette of the *Humicola lanuginosa* lipase is shown in FIG. 1 (SEQ ID NO:1). The restriction map of plasmid pAHL containing this expression cassette is shown in FIG. 2. The plasmid was used as template for construction of some of the *Humicola* lipase variants. The method used is described in the following and is further outlined in FIGS. 3 and 4. It was originally published by Nelson & Long in Analytical Biochemistry, 180,147–151 (1989).

Linearization of Plasmid pAHL

The circular plasmid pAHL was linearized with the restriction enzyme SphI in the following 50 μl reaction mixture; 50 mM NaCl, 10 mM Tris-HCl, pH 7.9, 10 mM MgCl$_2$, 1 mM dithiothreitol, 1 μg plasmid and 2 units of SphI. The digestion was carried out for 2 hours at 37° C. The reaction mixture was extracted with phenol (equilibrated with Tris-HCl), pH 7.5) and precipitated by adding 2 volumes of ice-cold 96% ethanol. After centrifugation and drying of the pellet, the linearized DNA was dissolved in 50 μl H$_2$O and the concentration estimated on an agarose gel.

3-Step PCR Mutagenesis

Figure 4:
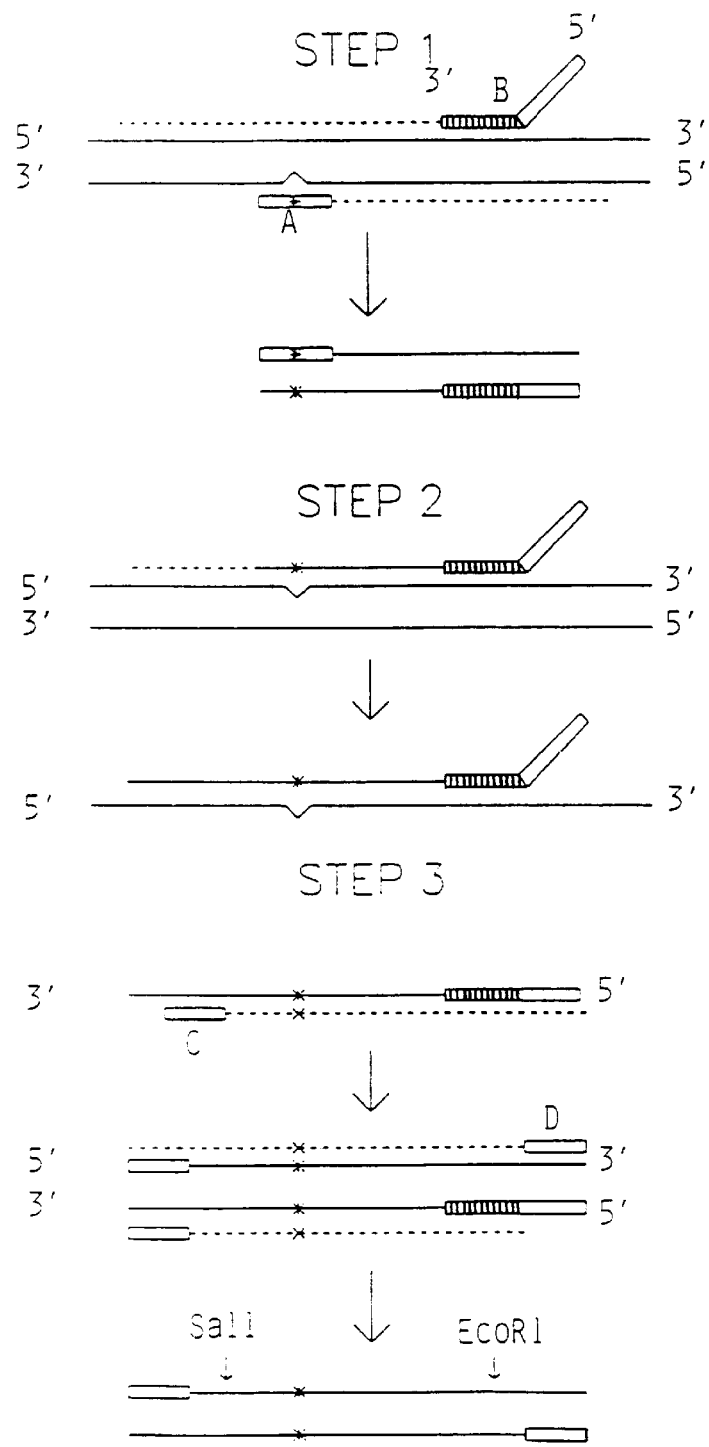

As is also shown in FIG. 4, 3-step mutagenisation involved the use of four primers:

Mutagenisation primer (=A):
5'-GGGGACAAGGGTTGGAGATTTGATCCA-3' (SEQ ID NO:5)

PCR Helper 1 (=B):
5'-GGTCATCCAGTCACTGAGACCCTCTACCTATTA-AATCGGC-3' (SEQ ID NO:6)

PCR Helper 2(=C):
5'-CCATGGCTTTCACGGTGTCT-3' (SEQ ID NO:7)

PCR Handle (=D):
5'GGTCATCCAGTCACTGAGAC-3' (SEQ ID NO:8)

All 3 steps were carried out in the following buffer containing: 10 mM Tris-HCl, pH 8.3, 50 mM KCl, 1.5 mM MgCl$_2$, 0.001% gelatin, 0.2 mM dATP, 0.2 mM dCTP, 0.2 mM dGTP, 0.2 mM TTP, 2.5 units Taq polymerase.

In step 1, 100 pmol primer A, 100 pmol primer b, and 1 fmol linearized plasmid were added to a total of 100 μl of the above buffer and 15 cycles consisting of 2 minutes at 95° C., 2 minutes at 37° C. and 3 minutes at 72° C. were carried out.

The concentration of the PCR product was estimated on a agarose gel. Then, step 2 was carried out. 0.6 pmol step 1 product and 1 fmol linearized plasmid were contained in a total of 100 μl of the previously mentioned buffer and 1 cycle consisting of 5 minutes at 95° C., 2 minutes at 37° C. and 10 minutes at 72° C. was carried out.

To the step 2 reaction mixture, 100 pmol primer C and 100 pmol primer D were added (1 μl of each) and 20 cycles consisting of 2 minutes at 95° C., 2 minutes at 37° C. and 3 minutes at 72° C. were carried out. This manipulation comprised step 3 in the mutagenisation procedure.

Isolation of Mutated Restriction Fragment

The product from step 3 was isolated from an agarose gel and re-dissolved in 20 μl H$_2$O. Then, it was digested with the restriction enzymes BstXI and BglII in a total volume of 50 μl with the following composition: 100 mM NaCl, 50 mM Tris-HCl, pH 7.9, 10 mM MgCl$_2$, 1 mM with DTT, 5 units of BglII and 10 units of BstXI. Incubation was at 37° C. for 2 hours. The 200 bp BstXI/BglII fragment was isolated from an agarose gel.

Ligation To Expression Vector pAHL

The expression plasmid pAHL was cleaved with BstXI and BglII under conditions indicated above and the large fragment was isolated from an agarose gel. To this vector, the mutated fragment isolated above was ligated and the ligation mix was used to transform *E. coli*. Sequence analysis was carried out on the double-stranded plasmid using the di-deoxy chain termination procedure developed by Sanger. The plasmid was named pAHLG225P and is identical to pAHL, except for the altered codon.

The plasmid was then ready to be transformed into the host organism. Preferred host organisms are of the genus *Aspergillus*. Transformation and expression are carried out essentially as described in European Patent Application No. 305,216, supra.

Construction of S224P, I241P, and T244P Variants

The plasmids pAHLS224P, pAHLI241P, and pAHLT244P, encoding *Humicola lanuginosa*S224P, *Humicola lanuginosa*/I241P, and *Humicola lanuginosa*/T244P, respectively, were constructed using the method described above, with the exception that the following primers were used an mutagenisation primer ("Primer A").

S224P: 5'-GACASGGGTTCCTGGTTTGATCCAGTA-3'(SEQ ID NO:9)

I241P: 5'-GCCGGTGGCATCTGGGCCTTCTATCTT-3' (SEQ ID NO:10)

T244P: 5'-TATTGCCGCCGGGGGCATCGATGCC-3' (SEQ ID NO:11)

EXAMPLE 2

Purification Example

About 200 ml of supernatant were centrifuged and precipitate was discarded by decanting. Slowly ice cold ethanol was added to the supernatant on ice bath. The precipitate was centrifuged and discarded and pH af the supernatant was adjusted to 7 with NaOH.

The 70% ethanol supernatant were applied on 200 ml DEAE fast flow sepharose column equilibrated with 50 mM Tris acetate buffer, pH 7, and flow rate 5 ml/min. The column was washed until $OD_{280}$ was less than 0.05. The bound protein was eluted with linear NaCl gradient up to 0.5 M NaCl in the same buffer, using 5 times column volume. The lipase activity was eluted between 0.1 and 0.15 M NaCl salt concentration.

The fractions containing the lipase activity were pooled and ammonium acetate was added to a final concentration of 0.8 M. The pool was applied on a Toyopearl™-Butyl column at a flow rate of 5 ml/min. The column was equilibrated with 0.8 M ammonium acetate and washed until $OD_{280}$ was below 0.05.

The bound activity was eluted with Mili-Q water. The fractions with lipase activity were pooled and the conductivity of the pool was adjusted to less than that of a 50 mM Tris acetate buffer, pH 7.

The pool was applied on a 30 ml HPQ-sepharose column equilibrated with 50 mM Tris acetate buffer, pH 7, at a flow rate of 1 ml/min. The bound activity was eluted with a linear salt gradient up to 1 M NaCl.

EXAMPLE 3

Differential Scanning Calorimetry

Purified lipase variants of the invention were subjected to thermal analysis by Differential Scanning Calorimetry (DSC). Using this technique, the thermal denaturation temperature, $T_d$, is determined by heating an enzyme solution at a constant programmed rate.

A Differential Scanning Calorimeter, MC-2D, from MicroCal Inc., was used for the investigations. Enzyme solutions were prepared in 50 mM TRIS-acetate, pH 7.0. Enzyme concentration ranged between 0.6 and 0.9 mg/ml, and a total volume of approximately 1.2 ml was used for each experiment. All samples were heated from 25° C. at a scan rate of 90° C./hour.

The results from this experiment are presented in Table 3 above.

Temperature Stability

The thermostability of a purified lipase variant of the invention was also tested by activity determination at 70° C.

Samples were diluted to 1 mg/ml using 0.1 M Tris buffer, pH 7.0. Test tubes containing 100 µl of enzyme solution were placed in a waterbath at 70° C. for 10, 25, and 45 minutes, respectively.

The residual activity (LU/mg) was measured using the analytical method described in this specification.

Figure 7:
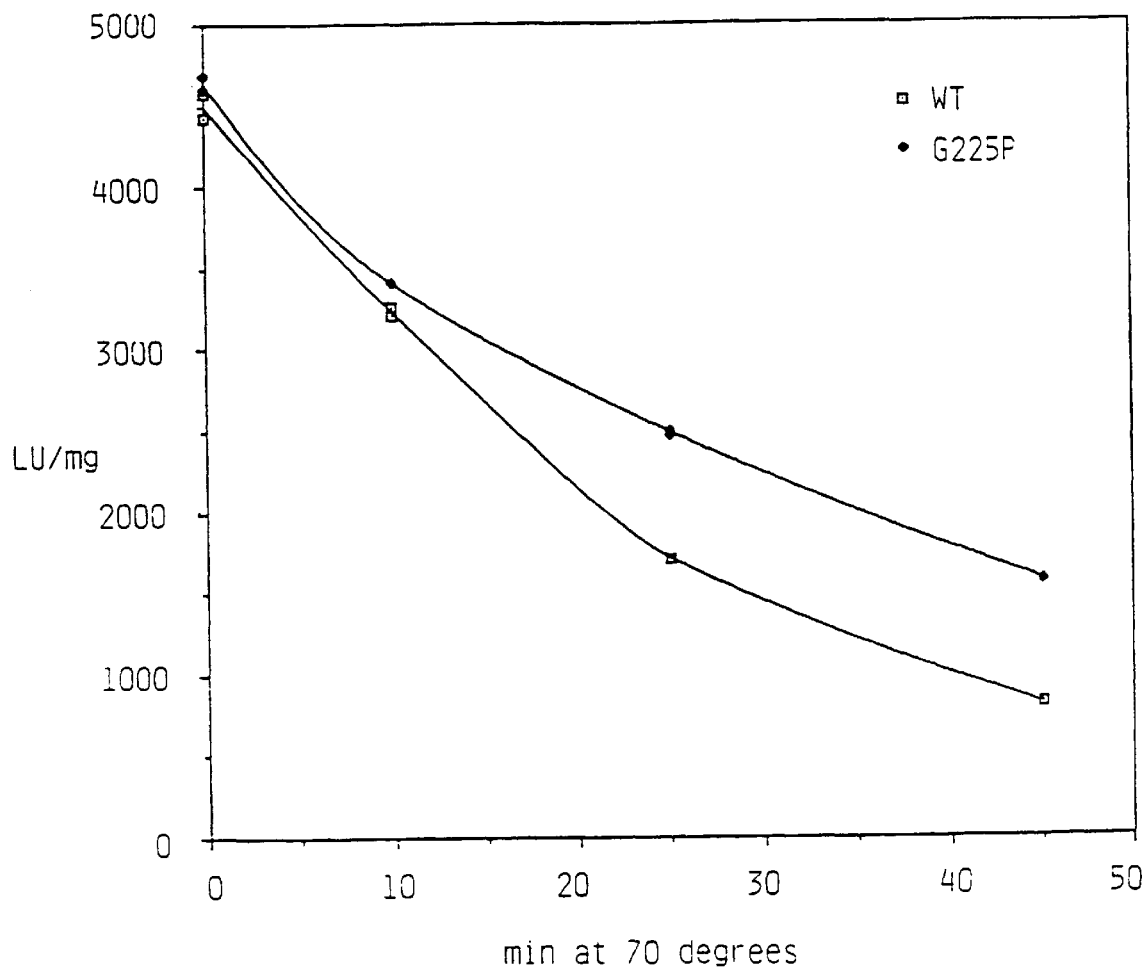
FIG. 7 shows the stability at 70° C. and pH 7 of Humicola lanuginosa/-G225P lipase (♦) of the invention compared to wildtype enzyme (□).

The results from this experiment are presented in FIG. 7.

---

We claim:

1. A mutant of a *Humicola lanuginosa* lipase, comprising a substitution of an amino acid residue other than proline with a proline residue at one or more positions; wherein the position is 225 or 244.

2. A mutant according to claim 1, wherein the position is 225.

3. A mutant according to claim 1, wherein the position is 244.

4. A mutant according to claim 1, wherein the lipase has an amino acid sequence of amino acid residues 1–269 of SEQ ID NO:2.

5. A nucleotide sequence encoding a mutant of claim 1.

6. An expression vector containing a nucleotide sequence of claim 5.

7. A host cell containing an expression vector according to claim 6.

8. A detergent composition comprising a mutant of claim 1 and a surfactant.

9. A detergent additive comprising a mutant of claim 1 in the form of a granulate liquid, a slurry, or a protected enzyme.

* * * * *